United States Patent
Ghodsalavi et al.

(10) Patent No.: US 12,336,542 B2
(45) Date of Patent: Jun. 24, 2025

(54) MEANS AND METHODS FOR IMPROVING PLANT GROWTH AND YIELD

(71) Applicants: APHEA.BIO NV, Zwijnaarde (BE); FUNDACIÓN CENTRO DE EXCELENCIA EN INVESTIGACIÓN DE MEDICAMENTOS INNOVADORES EN ANDALUCIA, MEDINA, Granada (ES)

(72) Inventors: Behnoush Ghodsalavi, Zwijnaarde (BE); Isabel Vercauteren, Zwijnaarde (BE); Steven Vandenabeele, Zwijnaarde (BE); Thomas Simon, Zwijnaarde (BE); Tom Viaene, Ghent (BE)

(73) Assignees: APHEA.BIO NV, Zwijnaarde (BE); FUNDACIÓN CENTRO DE EXCELENCIA EN INVESTIGACIÓN DE MEDICAMENTOS INNOVADORES EN ANDALUCIA, MEDINA, Granada (ES)

( * ) Notice: Subject to any disclaimer, the term of this patent is extended or adjusted under 35 U.S.C. 154(b) by 775 days.

(21) Appl. No.: 17/424,494

(22) PCT Filed: Feb. 10, 2020

(86) PCT No.: PCT/EP2020/053285
§ 371 (c)(1),
(2) Date: Jul. 20, 2021

(87) PCT Pub. No.: WO2020/161351
PCT Pub. Date: Aug. 13, 2020

(65) Prior Publication Data
US 2022/0087265 A1    Mar. 24, 2022

(30) Foreign Application Priority Data
Feb. 8, 2019 (EP) .................... 19156270

(51) Int. Cl.
*A01N 63/20* (2020.01)
*C12N 1/20* (2006.01)
*C12R 1/01* (2006.01)

(52) U.S. Cl.
CPC ............. *A01N 63/20* (2020.01); *C12N 1/205* (2021.05); *C12R 2001/01* (2021.05)

(58) Field of Classification Search
None
See application file for complete search history.

(56) References Cited

FOREIGN PATENT DOCUMENTS

| CN | 107557321 A | 1/2018 |
|---|---|---|
| WO | 2015035099 A1 | 3/2015 |
| WO | 2016200987 A1 | 12/2016 |
| WO | 2018045004 A1 | 3/2018 |
| WO | 2018060519 A1 | 4/2018 |

OTHER PUBLICATIONS

Challis et al. PNAS vol. 100(S2), pp. 14555-14561. (Year: 2003).*
Wahyudi et al. (Biodiversitas, 2019, p. 2547-2553).*
Aislabie et al., "Bacterial composition of soils of the Lake Wellman area, Darwin Mountains, Antarctica," Extremophiles, 2013, vol. 17, pp. 775-786.
Busarakam et al., "*Modestobacter caceresii* sp. nov., novel actinobacteria with an insight into their adaptive mechanisms for survival in extreme hyper-arid Atacama Desert soils," Systematic and Applied Microbiology, 2016, vol. 39, pp. 243-251.
Gontang et al., "Phylogenetic Diversity of Gram-Positive Bacteria Cultured from Marine Sediments," Applied and Environmental Microbiology, 2007, vol. 73, No. 10, pp. 3272-3282.
Lanoot et al., "Grouping of streptomycetes using 16S-ITS RFLP fingerprinting," Research in Microbiology, 2005, vol. 156, pp. 755-762.
Xiao et al., "*Modestobacter marinus* sp. nov., a psychrotolerant actinobacterium from deep-sea sediment, and emended description of the genus *Modestobacter*," International Journal of Systematic and Evolutionary Microbiology, 2011, vol. 61, pp. 1710-1714.
Fukuchi et al., "Rotihibins, Novel Plant Growth Regulators from Streptomyces graminofaciens," The Journal of Antibiotics, 1995, vol. 48, No. 9, pp. 1004-1010.
Girard et al., "A novel taxonomic marker that discriminates between morphologically complex actinomycetes," Open Biology, 2013, vol. 3, No. 10, 13 pages.
Guo et al., "A multilocus phylogeny of the Streptomyces griseus 16S rRNA gene clade: use of multilocus sequence analysis for streptomycete systematics," International Journal of Systematic and Evolutionary Microbiology, 2008, vol. 58, No. 1, pp. 149-159.
Varela Chaves et al., "Identification and Phylogeny of Streptomyces Based on Gene Sequences," Research Journal of Microbiology, 2018, vol. 13, No. 1, pp. 13-20.
WIPO, International Search Report for PCT/EP2020/053285, Jul. 6, 2020.

* cited by examiner

*Primary Examiner* — Agnieszka Boesen
(74) *Attorney, Agent, or Firm* — ArentFox Schiff LLP

(57) ABSTRACT

The current invention relates to a purified bacterial strain for improving plant growth and/or yield. The invention also relates to a bacterial population, a microbial active ingredient, an agriculturally active ingredient, a synthetic composition, and methods for improving plant growth and/or yield by improving a trait of agronomic importance in a plant and by conferring resistance to a plant pathogen infection.

10 Claims, 11 Drawing Sheets
Specification includes a Sequence Listing.

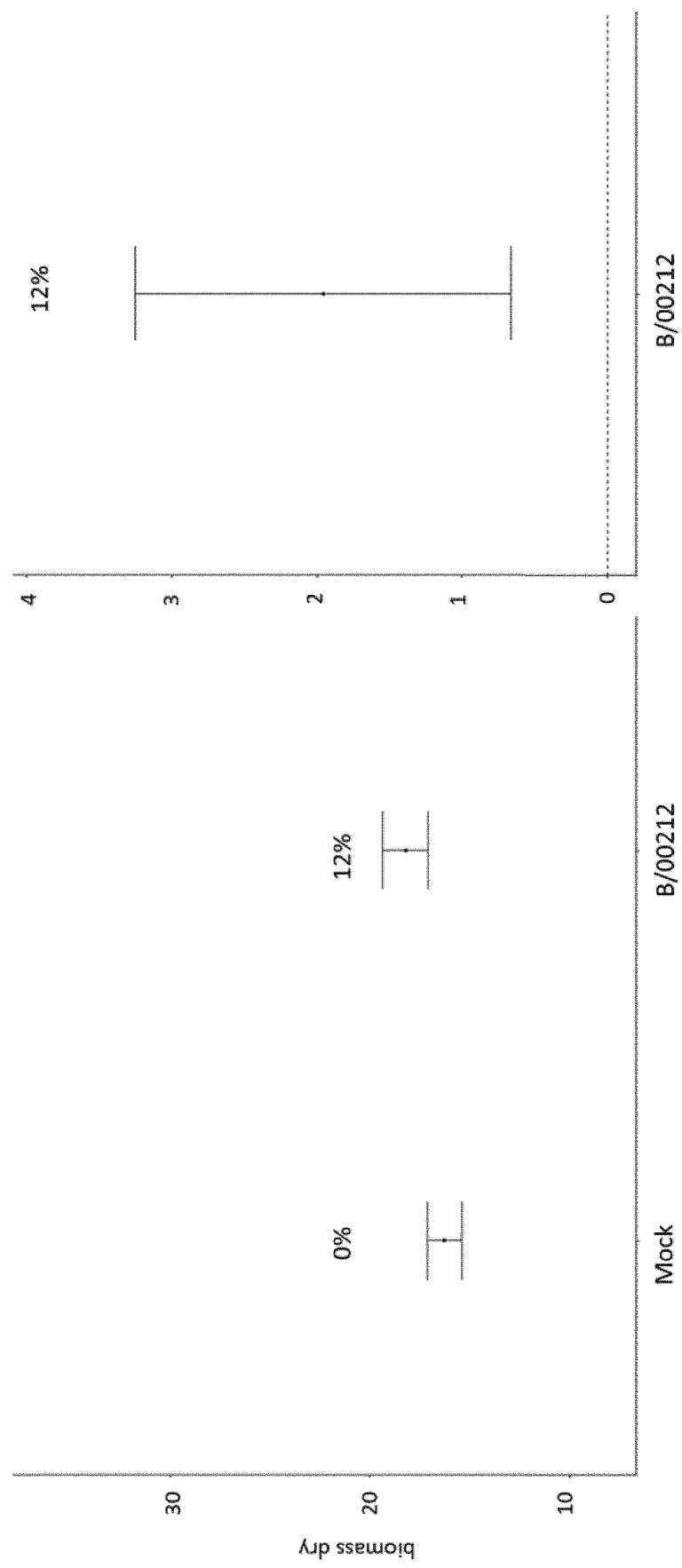

SEQUENCE LISTING

<160> NUMBER OF SEQ ID NOS: 13

<210> SEQ ID NO 1
<211> LENGTH: 1445
<212> TYPE: DNA
<213> ORGANISM: Modestobacter marinus

<400> SEQUENCE: 1

```
gacgaacgct ggcggcgtgc ttaacacatg caagtcgagc gaggcccatc cttcggggtg      60
gtgccctagc ggcgaacggg tgagtaacac gtgggcaacc tgccctcagc tctgggataa     120
ctccaagaaa ttggtgctaa taccggatgt gaccgctgac cgcatggtct ggtggtggaa     180
agattcatcg gctgaggatg ggcccgcggc ctatcagctt gttggtgggg tagtggccca     240
ccaaggcgac gacgggtagc cggcctgaga ggtgaccgg ccacactggg actgagacac      300
ggcccagact cctacgggag gcagcagtgg ggaatattgc gcaatgggcg gaagcctgac     360
gcagcgacgc cgcgtgaggg atgacggcct tcgggttgta aacctctttc agtagggacg     420
aagcgagagt gacggtacct acagaagaag caccggccaa ctacgtgcca gcagccgcgg     480
taatacgtag ggtgcaagcg ttgtccggaa ttattgggcg taaagagctc gtaggcggtc     540
tgtcgcgtcg gctgtgaaaa cccgaggctc aacctcgggc ctgcagtcga tacgggcaaa     600
ctagagtact gcaggggaga ctggaattcc tggtgtagcg gtgaaatgcg cagatatcag     660
gaggaacacc ggtggcgaag gcgggtctct gggcagtaac tgacgctgag gagcgaaagc     720
gtggggagcg aacaggatta gataccctgg tagtccacgc cgtaaacgtt gggcgctagg     780
tgtggggggcc attccacggt ctccgtgccg cagctaacgc attaagcgcc ccgcctgggg     840
agtacgccg caaggctaaa actcaaagga attgacgggg gcccgcacaa gcggcggagc     900
atgttgctta attcgatgca acgcgaagaa ccttacctag gcttgacatg cacggaaatc     960
tcgtagagat acgggtgcc tttggcgtcg tgcacaggtg gtgcatggtt gtcgtcagct    1020
cgtgtcgtga gatgttgggt taagtcccgc aacgagcgca accctcgttc tatgttgcca    1080
gcacgtgatg gtggggactc ataggagact gccggggtca actcggagga aggtggggat    1140
gacgtcaaat catcatgccc cttatgtcta gggctgcaaa catgctacaa tggccggtac    1200
aaagggctgc gataccgcga ggtggagcga atcccaaaaa gccggtctca gttcggattg    1260
gggtctgcaa ctcgacccca tgaagttgga gtcgctagta atcgcagatc agcaacgctg    1320
cggtgaatac gttcccgggc cttgtacaca ccgcccgtca cgtcacgaaa gtcggtaacg    1380
cccgaagccg gtggcccaac ccttgtggag ggagccgtcg aaggcgggat cggcgattgg    1440
gacga                                                                1445
```

<210> SEQ ID NO 2
<211> LENGTH: 1447
<212> TYPE: DNA
<213> ORGANISM: Micrococcus luteus

<400> SEQUENCE: 2

```
gatgaacgct ggcggcgtgc ttaacacatg caagtcgaac gatgaagccc agcttgctgg      60
gtggattagt ggcgaacggg tgagtaacac gtgagtaacc tgcccttaac tctgggataa     120
gcctgggaaa ctgggtctaa taccggatag gagcgcctac cgcatggtgg gtgttggaaa     180
gatttatcgg ttttggatgg actcgcggcc tatcagcttg ttggtgaggt aatggctcac     240
caaggcgacg acgggtagcc ggcctgagag ggtgaccggc cacactggga ctgagacacg     300
gcccagactc ctacgggagg cagcagtggg gaatattgca caatgggcga aagcctgatg     360
```

```
cagcgacgcc gcgtgaggga tgacggcctt cgggttgtaa acctctttca gtagggaaga      420
agcgaaagtg acggtacctg cagaagaagc accggctaac tacgtgccag cagccgcggt      480
aatacgtagg gtgcgagcgt tatccggaat tattgggcgt aaagagctcg taggcggttt      540
gtcgcgtctg tcgtgaaagt ccggggctta accccggatc tgcggtgggt acgggcagac      600
tagagtgcag tagggagac tggaattcct ggtgtagcgg tggaatgcgc agatatcagg       660
aggaacaccg atggcgaagg caggtctctg ggctgtaact gacgctgagg agcgaaagca      720
tggggagcga acaggattag ataccctggt agtccatgcc gtaaacgttg ggcactaggt      780
gtggggacca ttccacggtt ccgcgccgc agctaacgca ttaagtgccc cgcctgggga      840
gtacggccgc aaggctaaaa ctcaaaggaa ttgacggggg cccgcacaag cggcggagca      900
tgcggattaa ttcgatgcaa cgcgaagaac cttaccaagg cttgacatgt tcccgatcgc      960
cgtagagata cggtttcccc tttggggcgg gttcacaggt ggtgcatggt tgtcgtcagc     1020
tcgtgtcgtg agatgttggg ttaagtcccg caacgagcgc aaccctcgtt ccatgttgcc     1080
agcacgtaat ggtggggact catgggagac tgccgggtc aactcggagg aaggtgagga     1140
cgacgtcaaa tcatcatgcc ccttatgtct tgggcttcac gcatgctaca atggccggta     1200
caatggggttg cgatactgtg aggtggagct aatcccaaaa agccggtctc agttcggatt     1260
ggggtctgca actcgacccc atgaagtcgg agtcgctagt aatcgcagat cagcaacgct     1320
gcggtgaata cgttcccggg ccttgtacac accgcccgtc aagtcacgaa agttggtaac     1380
acccgaagcc ggtggcctaa cccttgtggg ggggagccgt cgaaggtggg accagcgatt     1440
gggacta                                                                1447

<210> SEQ ID NO 3
<211> LENGTH: 1454
<212> TYPE: DNA
<213> ORGANISM: Kocuria rhizophila

<400> SEQUENCE: 3
gacgaacgct ggcggcgtgc ttaacacatg caagtcgaac gctgaagctt ggtgcttgca       60
ctgggtggat gagtggcgaa cgggtgagta atacgtgagt aacctgccct tgactctggg      120
ataagcctgg gaaactgggt ctaatactgg atacgacatg tcaccgcatg gtggtgtgtg      180
gaaagggttt tactggtttt ggatgggctc acggcctatc agcttgttgg tggggtaatg      240
gctcaccaag gcgacgacgg gtagccggcc tgagagggtg accggccaca ctgggactga      300
gacacggccc agactcctac gggaggcagc agtggggaat attgcacaat gggcggaagc      360
ctgatgcagc gacgccgcgt gagggatgac ggccttcggg ttgtaaacct ctttcagcac      420
ggaagaagcg aaagtgacgg tacgtgcaga agaagcgccg gctaactacg tgccagcagc      480
cgcggtaata cgtagggcgc aagcgttgtc ggaattatt gggcgtaaag agctcgtagg      540
cggtttgtcg cgtctgctgt gaaagcccgg ggcttaaccc cggtgtgca gtgggtacgg      600
gcagacttga gtgcagtagg ggagactgga attcctggtg tagcggtgaa atgcgcagat      660
atcaggagga acaccgatgg cgaaggcagg tctctgggct gttactgacg ctgaggagcg      720
aaagcatggg gagcgaacag gattagatac cctggtagtc catgccgtaa acgttgggca      780
ctaggtgtgg ggaacattcc acgttttccg cgccgtagct aacgcattaa gtgccccgcc      840
tggggagtac ggccgcaagg ctaaaactca gaggaattga cggggcccg cacaagcggc      900
ggagcatgcg gattaattcg atgcaacgcg aagaacctta ccaaggcttg acatacaccg     960
```

```
gaccgggcca gagatggtct ttccccttg tggggctggt gtacaggtgg tgcatggttg    1020
tcgtcagctc gtgtcgtgag atgttgggtt aagtcccgca acgagcgcaa ccctcgttct    1080
atgttgccag cacgtgatgg tggggactca taggagactg ccggggtcaa ctcggaggaa    1140
ggtgaggatg acgtcaaatc atcatgcccc ttatgtcttg ggcttcacgc atgctacaat    1200
ggccagtaca atgggttgcg atgccgcgag gtggagctaa tcccaaaaag ctggtctcag    1260
ttcggatcgt ggtctgcaac tcgaccacgt gaagtcggag tcgctagtaa tcgcagatca    1320
gcaacgctgc ggtgaatacg ttcccgggcc ttgtacacac cgcccgtcaa gtcacgaaag    1380
ttggtaacac ccgaagccgg tggcctaacc cttgtggggg gagccgtcga aggtgggact    1440
ggcgattggg acta                                                       1454

<210> SEQ ID NO 4
<211> LENGTH: 1401
<212> TYPE: DNA
<213> ORGANISM: Modestobacter marinus

<400> SEQUENCE: 4
taccatgcag tcgagcgagg cccatccttc ggggtggtgc cctagcggcg aacgggtgag      60
taacacgtgg gcaacctgcc ctcagctctg ggataactcc aagaaattgg tgctaatacc     120
ggatgtgacc gctgaccgca tggtctggtg gtggaaagat tcatcggctg aggatgggcc     180
cgcggcctat cagcttgttg gtggggtaat ggcccaccaa ggcgacgacg ggtagccggc     240
ctgagagggt gaccggccac actgggactg agacacggcc cagactccta cgggaggcag     300
cagtggggaa tattgcgcaa tgggcgaaag cctgacgcag cgacgccgcg tgagggatga     360
cggccttcgg gttgtaaacc tctttcagta gggacgaagc gaaagtgacg gtacctacag     420
aagaagcacc ggccaactac gtgccagcag ccgcggtaat acgtagggtg caagcgttgt     480
ccggaattat tgggcgtaaa gagctcgtag gcggtctgtc gcgtcggctg tgaaaacccg     540
aggctcaacc tcgggcctgc agtcgatacg ggcaaactag agtactgcag gggagactgg     600
aattcctggt gtagcggtga aatgcgcaga tatcaggagg aacaccggtg gcgaaggcgg     660
gtctctgggc agtaactgac gctgaggagc gaaagcgtgg ggagcgaaca ggattagata     720
ccctggtagt ccacgccgta aacgttgggc gctaggtgtg ggggccattc cacggtctcc     780
gtgccgcagc taacgcatta agcgccccgc ctggggagta cggccgcaag gctaaaactc     840
aaaggaattg acggggcccc gcacaagcgg cggagcatgt tgcttaattc gatgcaacgc     900
gaagaacctt acctaggctt gacatgcacg gaaatctcgt agagatacgg ggtgcctttg     960
gcgtcgtgca caggtggtgc atggttgtcg tcagctcgtg tcgtgagatg ttgggttaag    1020
tcccgcaacg agcgcaaccc tcgttctatg ttgccagcac gtgatggtgg ggactcatag    1080
gagactgccg gggtcaactc ggaggaaggt ggggatgacg tcaaatcatc atgcccctta    1140
tgtctagggc tgcaaacatg ctacaatggc cggtacaaag ggctgcgata ccgcgaggtg    1200
gagcgaatcc caaaaagccg gtctcagttc ggattgggt ctgcaactcg accccatgaa    1260
gttggagtcg ctagtaatcg cagatcagca acgctgcggt gaatacgttc ccgggccttg    1320
tacacaccgc ccgtcacgtc acgaaagtcg taacgcccg aagccggtgg cccaacccct    1380
gtggagggag ccgtcgaagc g                                              1401

<210> SEQ ID NO 5
<211> LENGTH: 1441
<212> TYPE: DNA
<213> ORGANISM: Kribbella qitaiheensis
```

<400> SEQUENCE: 5

```
gacgaacgct ggcggcgtgc ttaacacatg caagtcgagc ggtaaggctc cttcggggt    60
acacgagcgg cgaacgggtg agtaacacgt gagcaaccta ccctcaactt cgggataagc   120
ctcggaaacg gggtctaata ccggatatca ctcttggttt catgaccggg ggttgaaagt   180
tctggcggtt ggggatgggc tcgcggccta tcagcttgtt ggtggggtaa tggcctacca   240
aggcgtcgac gggtagccgg cctgagaggg cgaccggcca cactgggact gagacacggc   300
ccagactcct acgggaggca gcagtgggga atattgcgca atgggcgaaa gcctgacgca   360
gcaacgccgc gtgagggatg acggccttcg ggttgtaaac ctctttcagc agggacgaag   420
cgagagtgac ggtacctgca gaagaaggac cggccaacta cgtgccagca gccgcggtaa   480
tacgtagggt ccgagcgttg tccggaatta ttgggcgtaa agggctcgta ggcggttcgt   540
cacgtcggga gtgaaaactc ggagcttaac tccgagcctg cttccgatac gggcagacta   600
gaggtaggca ggggagagcg gaactcctgg tgtagcggtg aatgcgcag atatcaggaa     660
gaacaccggt ggcgaaggcg gctctctggg ccttacctga cgctgaggag cgaaagcgtg   720
ggtagcgaac aggattagat accctggtag tccacgccgt aaacgttggg cgctaggtgt   780
gggggacatt ccacgtcctc cgtgccgcag ctaacgcatt aagcgcccg cctggggagt    840
acggccgcaa ggctaaaact caaaggaatt gacgggggcc cgcacaagcg cggagcatg    900
cggattaatt cgatgcaacg cgaagaacct tacctgggtt tgacatatag ggaaatcctc   960
cagagatggg gggtccgtaa gggtcctata caggtggtgc atggctgtcg tcagctcgtg  1020
tcgtgagatg ttgggttaag tcccgcaacg agcgcaaccc tcgtcctatg ttgccagcac  1080
gttatggtgg ggactcatag gagactgccg ggtcaactc ggaggaaggt ggggatgacg    1140
tcaagtcatc atgccccta tgtccagggc ttcacgcatg ctacaatggc cggtacaaag   1200
ggctgcgaaa ccgcaaggtg gagcgaatcc caaaaagccg gtctcagttc ggattggggt  1260
ctgcaactcg accccatgaa gtcggagtcg ctagtaatcg cagatcagca acgctgcggt  1320
gaatacgttc ccgggccttg tacacaccgc ccgtcacgtc atgaaagtcg gcaacacccg  1380
aagccggtgg cctaaccctt gtggagggag ccgtcgaagg tggggctggc gattaggacg  1440
a                                                                  1441
```

<210> SEQ ID NO 6
<211> LENGTH: 1312
<212> TYPE: DNA
<213> ORGANISM: Nocardiopsis dassonvillei

<400> SEQUENCE: 6

```
ttaccatgca gtcgagcggt aaggcccttc ggggtacacg agcggcgaac gggtgagtaa    60
cacgtgagca acctgcccct gactctggga taagcggtgg aaacgccgtc taataccgga   120
tacgacccgc cacctcatgg tggagggtgg aaagtttttc ggtcagggat gggctcgcgg   180
cctatcagct tgttggtggg gtaacggcct accaaggcga ttacgggtag ccggcctgag   240
agggcgaccg gccacactgg gactgagaca cggcccagac tcctgcggga gcagcagtg    300
gggaatattg cgcaatgggc gaaagcctga cgcagcgacg ccgcgtgggg gatgacggcc   360
ttcgggttgt aaacctcttt taccaccaac gcaggcttcc agttctctgg aggttgacgg   420
taggtgggga ataaggaccg gctaactacg tgccagcagc cgcggtaata cgtagggtcc   480
gagcgttgtc cggaattatt gggcgtaaag agctcgtagg cggcgtgtcg cgtctgctgt   540
```

```
gaaagaccgg ggcttaactc cggttctgca gtggatacgg gcatgctaga ggtaggtagg      600
ggagactgga attcctggtg tagcggtgaa atgcgcagat atcaggagga acaccggtgg      660
cgaaggcggg tctctgggcc ttacctgacg ctgaggagcg aaagcatggg gagcgaacag      720
gaattagata ccctggtagt ccatgccgta acgttgggc gctaggtgtg gggactttcc       780
acggtttccg cgccgtagct aacgcattaa gcgccccgcc tggggagtac ggccgcaagg      840
ctaaaactca aaggaattga cggggcccca cacaagcggc ggagcatgtt gcttaattcg      900
acgcaacgcg aagaacctta ccaaggtttg acatcacccg tggactcgca gagatgtgag      960
gtcatttagt tggcgggtga caggtggtgc atggctgtcg tcagctcgtg tcgtgagatg     1020
ttgggttaag tcccgcaacg agcgcaaccc ttgttccatg ttgccagcac gtaatggtgg     1080
ggactcatgg gagactgccg gggtcaactc ggaggaaggt ggggatgacg tcaagtcatc     1140 atgccccta tgtcttgggc tgcaaacatg ctacaatggc cggtacaatg ggcgtgcgat      1200
accgtaaggt ggagcgaatc cctaaaagcc ggtctcagtt cggattgggg tctgcaactc     1260
gaccccatga aggtggagtc gctagtaatc gcggatcagc aacgccgcgg tg            1312
```

<210> SEQ ID NO 7
<211> LENGTH: 1409
<212> TYPE: DNA
<213> ORGANISM: Streptomyces graminofaciens

<400> SEQUENCE: 7

```
cacatgcaag tcgaacgatg aagcccttcg gggtggatta gtggcgaacg ggtgagtaac       60
acgtgggcaa tctgcccttc actctgggac aagccctgga acggggtct aataccggat       120 aacactgcgg atcgcatggt ctgcggttga agctccggc ggtgaaggat gagcccgcgg       180
cctatcagct tgttggtggg gtgatggcct accaaggcga cgacgggtag ccggcctgag      240
agggcgaccg gccacactgg gactgagaca cggcccagac tcctacggga ggcagcagtg      300
gggaatattg cacaatgggc gaaagcctga tgcagcgacg ccgcgtgagg gatgacggcc      360
ttcgggttgt aaacctcttt cagcagggaa gaagcgaaag tgacggtacc tgcagaagaa      420
gcgccggcta actacgtgcc agcagccgcg gtaatacgta gggcgcaagc gttgtccgga      480
attattgggc gtaaagagct cgtaggcggc ttgtcacgtc ggatgtgaaa gcccggggct      540 taacccggg tctgcattcg atacgggcag gctagagtgt ggtaggggag atcggaattc       600
ctggtgtagc ggtgaaatgc gcagatatca ggaggaacac cggtggcgaa ggcggatctc      660
tgggccatta ctgacgctga ggagcgaaag cgtgggagc gaacaggatt agataccctg       720
gtagtccacg ccgtaaacgt tgggaactag gtgttggcga cattccacgt cgtcggtgcc      780
gcagctaacg cattaagttc cccgcctggg gagtacggcc gcaaggctaa gactcaaagg      840
aattgacggg ggcccgcaca agcagcggag catgtggctt aattcgacgc aacgcgaaga      900
accttaccaa ggcttgacat ataccggaaa gcatcagaga tggtgccccc cttgtggtcg      960
gtatacaggt ggtgcatggc tgtcgtcagc tcgtgtcgtg agatgttggg ttaagtcccg     1020
caacgagcgc aaccccttgtt ctgtgttgcc agcatgccct tcggggtgat ggggactcac     1080
aggagactgc cggggtcaac tcggaggaag gtggggacga cgtcaagtca tcatgcccct     1140
tatgtcttgg gctgcacacg tgctacaatg gccggtacaa agagctgcga tgccgcgagg     1200
cggagcgaat ctcaaaaagc cggtctcagt tcggattggg gtctgcaact cgaccccatg     1260
aagtcggagt tgctagtaat cgcagatcag cattgctgcg gtgaatacgt tcccgggcct     1320
tgtacacacc gcccgtcacg tcacgaaagt cggtaacacc cgaagccggt ggcccaaccc     1380
```

```
                                        cttgtgggag ggagctgtcg aagtgacct                    1409

<210> SEQ ID NO 8
<211> LENGTH: 1407
<212> TYPE: DNA
<213> ORGANISM: Streptomyces ramulosus

<400> SEQUENCE: 8
attcgacgat tccctcccac aagggttgg gccaccggct tcgggtgtta ccgactttcg         60
tgacgtgacg ggcggtgtgt acaaggcccg ggaacgtatt caccgcagca atgctgatct      120
gcgattacta gcaactccaa cttcatgggg tcgagttgca gaccccaatc cgaactgaga      180
ccggcttttt gagattcgct ccacctcacg gcttcgcagc tcattgtacc ggccattgta      240
gcacgtgtgc agcccaagac ataaggggca tgatgacttg acgtcgtccc caccttcctc      300
cgagttgacc ccggcagtct cctgtgagtc cccatcaccc gaaaggcat gctggcaaca       360
cagaacaagg gttgcgctcg ttgcgggact taacccaaca tctcacgaca cgagctgacg      420
acagccatgc accacctgta caccgaccac aaggggcgc ctgtctccag acgtttccgg       480
tgtatgtcaa gccttggtaa ggttcttcgc gttgcgtcga attaagccac atgctccgct      540
gcttgtgcgg gcccccgtca attcctttga gttttagcct tgcggccgta ctccccaggc      600
ggggaactta atgcgttagc tgcggcacgg acaacgtgga atgtcgccca cctagttc       660
ccaacgttta cggcgtggac taccagggta tctaatcctg ttcgctcccc acgctttcgc      720
tcctcagcgt cagtatcggc ccagagatcc gccttcgcca ccggtgttcc tcctgatatc      780
tgcgcatttc accgctacac caggaattcc gatctcccct accgaactct agcctgcccg      840
tatcgaatgc agacccgggg ttaagccccg ggctttcaca tccgacgcga caagccgcct      900
acgagctctt tacgcccaat aattccggac aacgcttgcg ccctacgtat taccgcggct     960
gctggcacgt agttagccgg cgcttcttct gcaggtaccg tcactctcgc ttcttccctg     1020
ctgaaagagg tttacaaccc gaaggccgtc atccctcacg cggcgtcgct gcatcaggct     1080
ttcgcccatt gtgcaatatt ccccactgct gcctcccgta ggagtctggg ccgtgtctca     1140
gtcccagtgt ggccggtcgc cctctcaggc cggctacccg tcgtcgcctt ggtaggccat     1200
cacccccacca acaagctgat aggccgcggg ctcatcctgc accgccggag ctttccacca    1260
ccagaccatg cggccggtag tcatatccgg tattagaccc cgtttccagg gcttgtccca     1320
gagtgcaggg cagattgccc acgtgttact caccgttcg ccactaatcc cccaccgaag     1380
tcgggttcat cgttcgactt gcatggt                                            1407

<210> SEQ ID NO 9
<211> LENGTH: 1255
<212> TYPE: DNA
<213> ORGANISM: Crossiella cryophila

<400> SEQUENCE: 9
gcttggtggt ggaaagttcc ggcggtgcag gatgggcccg cggcctatca gcttgttggt        60
ggggtaatgg cctaccaagg cgacgacggg tagccggcct gagagggcga ccggccacac      120
tgggactgag acacggccca gactcctacg ggaggcagca gtgggaata ttgcgcaatg       180
ggcgaaagcc tgacgcagcg acgccgcgtg agggatgacg gccttcgggt tgtaaacctc      240
tttcagtgcc gacgaagcga aagtgacggt aggtacagaa gaagcaccgg ccaactacgt      300
gccagcagcc gcggtaatac gtagggtgcg agcgttgtcc ggaattattg ggcgtaaaga      360
```

```
gctcgtaggc ggtttgttgc gtcggctgtg aaaactcggg gcttaactct gagcttgcag      420
tcgatacggg cagacttgag ttcggcaggg gagactggaa ttcctggtgt agcggtgaaa      480
tgcgcagata tcaggaggaa caccggtggc gaaggcgggt ctctgggccg atactgacgc      540
tgaggagcga aagcgtgggg agcgaacagg attagatacc ctggtagtcc acgccgtaaa      600
cgttgggcgc taggtgtggg ggtcattcca cggcctccgt gccgcagcta acgcattaag      660
cgccccgcct ggggagtacg gccgcaaggc taaaactcaa aggaattgac ggggccccgc      720
acaagcggcg gagcatgtgg attaattcga tgcaacgcga agaaccttac ctgggcttga      780
catacaccgg aaacctgcag agatgtaggc cccttgtgg tcggtgtaca ggtggtgcat       840
ggctgtcgtc agctcgtgtc gtgagatgtt gggttaagtc ccgcaacgag cgcaacccTC      900
gttccatgtt gccagcgcgt aatggcgggg actcatggga gactgccggg gtcaactcgg      960
aggaaggtgg ggatgacgtc aagtcatcat gcccccttatg tccagggctt cacacatgct     1020
acaatggccg gtacaatggg ctgctaagcc gtgaggtgga gcgaatccct aaaagcggt      1080 ctcagttcgg atcggggtct gcaactcgac cccgtgaagt tggagtcgct agtaatcgca     1140
gatcagcaac gctgcggtga atacgttccc gggccttgta cacaccgccc gtcacgtcac     1200
gaaagtcggt aacacccgaa gcccatggcc caacccgtaa gggggggagt gtcga          1255
```

<210> SEQ ID NO 10
<211> LENGTH: 1390
<212> TYPE: DNA
<213> ORGANISM: Micromonospora carbonacea

<400> SEQUENCE: 10

```
attcgacggc tccctccaca agggttgggc caccggcttc gggtgttgcc gactttcgtg       60
acgtgacggg cggtgtgtac aaggcccggg aacgtattca ccgcagcgtt gctgatctgc      120
gattactagc gactccgact tcacggggtc gagttgcaga ccccgatccg aactgagacc      180
ggcttttTGG gattcgctcc acctcacggt atcgcagccc attgtaccgg ccattgtagc      240
atgcgtgaag ccctggacat aagggcatg atgacttgac gtcatcccca ccttcctccg      300
agttgacccc ggcagtcttc gatgagtccc cgccataacg cgctggcaac atcgaacgag      360
ggttgcgctc gttgcgggac ttaacccaac atctcacgac acgagctgac gacagccatg      420
caccacctgt gaccgccccc gaaggacccc ccatctctgg aggttttgcg gccatgtcaa      480
acccaggtaa ggttcttcgc gttgcatcga attaatccgc atgctccgcc gcttgtgcgg      540 gccccgtca attcctttga gttttagcct tgcggccgta ctcccaggc ggggcgctta       600 atgcgttagc tgcggcacag agaaccggag aggccccca cacctagcgc ccaacgttta      660
cagcgtggac taccagggta tctaatcctg ttcgctcccc acgctttcgc tcctcagcgt      720
cagtatcggc ccagagaccc gccttcgcca ccggtgttcc tcctgatatc tgcgcattTC      780
accgctacac caggaattcc agtctcccct accgaactct agcctgcccg tatcgaccgc      840
aggcttgggg ttgagcccca gttttcacg gtcgacgcga caagccgcct acgagctctt      900
tacgcccaat aaatccggac aacgctcgcg ccctacgtct taccgcggct gctggcacgt      960
agttggccgc cgcttcttct gcaggtaccg tcacttgcgc ttcgtccctg ctgaaagagg     1020
tttacaaccc gaaggccgtc atccctcacg cggcgtcgct gcatcaggct tccgcccatt     1080
gtgcaatatt ccccactgct gcctcccgta ggagtctggg ccgtgtctca gtcccagtgt     1140
ggccggtcgc cctctcaggc cggctacccg tcgtcgcctt ggtaggccat cacccccacca     1200 acaagctgat aggccgcgag cccatcccag gccgaaaaac tttccacccc cagtcatgcg     1260
```

| | |
|---|---|
| accaaaggtt gtatccggta ttagcccccg tttccgaggg ttatcccaaa gcctagggca | 1320 |
| ggttgctcac gtgttactca cccgttcgcc gctcgagtac cccgaagggc cttccgctcg | 1380 |
| acttgcatgg | 1390 |

<210> SEQ ID NO 11
<211> LENGTH: 1397
<212> TYPE: DNA
<213> ORGANISM: Streptomyces camponoticapitis

<400> SEQUENCE: 11

| | |
|---|---|
| ttcgacgctc cctcccacaa ggggttgggc caccggcttc gggtgttacc gactttcgtg | 60 |
| acgtgacggg cggtgtgtac aaggcccggg aacgtattca ccgcagcaat gctgatctgc | 120 |
| gattactagc aactccgact tcatggggtc gagttgcaga ccccaatccg aactgagacc | 180 |
| ggcttttga gattcgctcc accttgcggt atcgcagctc attgtaccgg ccattgtagc | 240 |
| acgtgtgcag cccaagacat aaggggcatg atgacttgac gtcgtcccca ccttcctccg | 300 |
| agttgacccc ggcggtctcc tgtgagtccc catcaccccg aagggcatgc tggcaacaca | 360 |
| gaacaagggt tgcgctcgtt gcgggactta acccaacatc tcacgacacg agctgacgac | 420 |
| agccatgcac cacctgtaca ccgaccacaa gggggcacc atctctgatg ctttccggtg | 480 |
| tatgtcaagc cttggtaagg ttcttcgcgt tgcgtcgaat taagccacat gctccgctgc | 540 |
| ttgtgcgggc ccccgtcaat tcctttgagt tttagccttg cggccgtact ccccaggcgg | 600 |
| ggaacttaat gcgttagctg cggcaccgac gacgtggaat gtcgccaaca cctagttccc | 660 |
| aacgtttacg gcgtggacta ccagggtatc taatcctgtt cgctccccac gctttcgctc | 720 |
| ctcagcgtca gtaatggccc agagatccgc cttcgccacc ggtgttcctc ctgatatctg | 780 |
| cgcatttcac cgctacacca ggaattccga tctcccctac cacactctag tctgcccgta | 840 |
| tcgaatgcag acccgggggtt aagcccccggg cttcacacc cgacgtgaca aaccgcctac | 900 |
| gagctctta cgcccaataa ttccggacaa cgcttgcgcc ctacgtatta ccgcggctgc | 960 |
| tggcacgtag ttagccggcg cttcttctgc aggtaccgtc actttcgctt cttccctgct | 1020 |
| gaaagaggtt tacaacccga aggccgtcat ccctcacgcg cgtcgctgc atcaggcttt | 1080 |
| cgcccattgt gcaatattcc ccactgctgc ctcccgtagg agtctgggcc gtgtctcagt | 1140 |
| cccagtgtgg ccggtcgccc tctcaggccg gctaccgtc gtcgccttgg taggccatta | 1200 |
| ccccaccaac aagctgatag gccgcgggct catcctgcac cgccggagct tttaaccatc | 1260 |
| ccccatgagg ggcacagtat tatccggtat tagacccgt ttccagggct tgtcccagag | 1320 |
| tgcagggcag attgcccacg tgttactcac ccgttcgcca ctaatccacc cgaaggcttc | 1380 |
| atcgttcgac ttgcatg | 1397 |

<210> SEQ ID NO 12
<211> LENGTH: 1395
<212> TYPE: DNA
<213> ORGANISM: Streptomyces caeruleus

<400> SEQUENCE: 12

| | |
|---|---|
| aagctccctc ccacaagggg ttggaccacc ggcttcgggt gttaccgact tcgtgacgt | 60 |
| gacgggcggt gtgtacaagg cccgggaacg tattcaccgc agcaatgctg atctgcgatt | 120 |
| actagcaact ccgacttcat ggggtcgagt tgcagacccc aatccgaact gagaccggct | 180 |
| ttttgagatt cgctccacct tgcggtatcg cagctcattg taccggccat tgtagcacgt | 240 |

```
gtgcagccca agacataagg ggcatgatga cttgacgtcg tccccacctt cctccgagtt      300
gaccccggcg gtctcctgtg agtccccatc accccgaagg gcatgctggc aacacagaac      360
aagggttgcg ctcgttgcgg gacttaaccc aacatctcac gacacgagct gacgacagcc      420
atgcaccacc tgtacaccga ccacaagggg ggcaccatct ctgatgcttt ccggtgtatg      480
tcaagccttg gtaaggttct tcgcgttgcg tcgaattaag ccacatgctc cgctgcttgt      540
gcgggccccc gtcaattcct ttgagtttta gccttgcggc cgtactcccc aggcggggaa      600
cttaatgcgt tagctgcggc accgacgacg tggaatgtcg ccaacaccta gttcccaacg      660
tttacgcgcg ggactaccag ggtatctaat cctgttcgct ccccacgctt tcgctcctca      720
gcgtcagtaa tggcccagag atccgccttc gccaccggtg ttcctcctga tatctgcgca      780
tttcaccgct acaccaggaa ttccgatctc ccctaccaca ctctagtctg cccgtatcga      840
atgcagaccc ggggttaagc cccgggcttt cacacccgac gtgacaaacc gcctacgagc      900
tctttacgcc caataattcc ggacaacgct tgcgccctac gtattaccgc ggctgctggc      960
acgtagttag ccggcgcttc ttctgcaggt accgtcactt tcgcttcttc cctgctgaaa     1020
gaggtttaca acccgaaggc cgtcatccct cacgcggcgt cgctgcatca ggctttcgcc     1080
cattgtgcaa tattccccac tgctgcctcc cgtaggagtc tgggccgtgt ctcagtccca     1140
gtgtggccgg tcgccctctc aggccggcta cccgtcgtcg ccttggtagg ccattacccc     1200
accaacaagc tgataggccg cgggctcatc ctgcaccgcc ggagctttca accgtccccc     1260
atgaggggca cagtattatc cggtattaga ccccgtttcc agggcttgtc ccagagtgca     1320
gggcagattg cccacgtgtt actcacccgt tcgccactaa tccacccgaa ggctcatcgt     1380
tcgactgcag gtaag                                                      1395

<210> SEQ ID NO 13
<211> LENGTH: 1020
<212> TYPE: DNA
<213> ORGANISM: Micromonospora eburnea

<400> SEQUENCE: 13
ctattcgacg gctccctcca caagggttgg gccaccggct tcgggtgttg ccgactttcg       60
tgacgtgacg ggcggtgtgt acaaggcccg ggaacgtatt caccgcagcg ttgctgatct      120
gcgattacta gcgactccga cttcacgggg tcgagttgca gaccccgatc cgaactgaga      180
ccggcttttt gggattcgct ccacctcacg gtatcgcagc ccattgtacc ggccattgta      240
gcatgcgtga agccctggac ataaggggca tgatgacttg acgtcatccc caccttcctc      300
cgagttgacc ccggcagtct tcgatgagtc cccgccataa cgcgctggca acatcgaacg      360
agggttgcgc tcgttgcggg acttaaccca acatctcacg acacgagctg acgacagcca      420
tgcaccacct gtgaccgccc ccgaaggacc ccacatctct gcaggttttg cggccatgtc      480
aaacccaggt aaggttcttc gcgttgcatc gaattaatcc gcatgctccg ccgcttgtgc      540
gggcccccgt caattccttt gagttttagc cttgcggccg tactcccag gcggggcgct      600 taatgcgtta gctgcggcac agggaaccgg agaggccccc cacacctagc gcccaacgtt      660
tacagcgtgg actaccaggg tatctaatcc tgttcgctcc ccacgctttc gctcctcagc      720
gtcagtatcg gcccagagac ccgccttcgc caccggtgtt cctcctgata tctgcgcatt      780
tcaccgctac accaggaatt ccagtctccc ctaccgaact ctagcctgcc cgtatcgact      840
```

```
gcaggcccgc ggttgagccg cgggttttca cagtcgacgc gacaagccgc ctacgagctc    900
tttacgccca ataaatccgg acaacgctcg cgccctacgt cttaccgcgg ctgctggcac    960
gtagttggcc ggcgcttctt ctgcaggtac cgtcacttac gcttcgtccc tgctgaaaga   1020
```

MEANS AND METHODS FOR IMPROVING PLANT GROWTH AND YIELD

FIELD OF THE INVENTION

The invention relates to the fields of plant biology and bacterial strains. More specifically, the invention provides novel bacterial strains which provide beneficial features to the plant upon colonization of the same. In particular, the compositions and methods disclosed herein are useful for enhancing plant growth and/or yield.

BACKGROUND

There is a need for improved agricultural plants that will enable the food production demands with fewer resources and more environmentally sustainable inputs, for plants with improved responses to various biotic and abiotic stresses.

Crop performance is optimized primarily via technologies directed towards the interplay between crop genotype (e.g. plant breeding, genetically-modified (GM) crops) and its surrounding environment (e.g. fertilizer, synthetic herbicides, pesticides). While these paradigms have assisted in the increasing global food production, yield growth rates have stalled in many major crops. Shifts in the climate are linked to production instabilities as well as changing pest and disease pressures. In addition, genetically manipulated (GM) crops and agrochemicals have challenged their use in a large number of agricultural important crops and countries, resulting in a lack of acceptance for many GM traits and the exclusion of GM crops and many agrochemicals from global markets. Therefor there is an urgent need for novel solutions to crop improvement, more particularly, there is a need for innovative, effective, environmentally-sustainable, and publicly-acceptable approaches to improve the growth, yield, and other agronomically important characteristics of plants.

A promising practice is the use of microorganisms that enhance plant growth and yield, increase tolerance to unfavorable conditions, or improve the resource use efficiency. In particular, a vast array of bacteria that live both within and around the plant tissues support the plant's health and growth.

WO 2016 200 987 discloses methods and compositions for providing a benefit to a plant by associating the plant with a beneficial endophyte of the genus *Streptomyces*. In particular, the invention relates to compositions and methods of improving soybean and maize plants.

WO 2015 035 099 relates to methods and materials for providing a benefit to a seed or seedling of an agricultural plant, in particular Glycine agricultural plants.

WO 2018 060 519 discloses methods and compositions for enhancing growth and/or yield of a plant by associating the plant with isolated bacterial strains of the genus *Streptomyces* or *Arthrobacter*. The plant is an agricultural plant, preferably a wheat or maize plant.

Gontang et al. 2007, Xiao et al. 2010, Aislabie et al. 2013, and Kanungnid et al. 2016 disclose the isolation and/or characterization of bacterial species from different sediments. However, these studies are not directed to the use of the bacterial species described therein for crop protection or improvement of plant growth and/or yield.

Bacteria influence plant growth through multiple mechanisms, and in some cases through interactions with other bacteria. Specific bacterial strains inhabit various host plant tissues and have been isolated from plant leaves, stems, and roots. Several bacteria have been disclosed that increase plant growth and/or reduce susceptibility to diseases caused by fungi, bacteria, viruses or other plant pathogens.

However, to successfully enhance the growth and/or yield of a plant, the purified bacterial strain has to maintain a critical population mass in the plant element, or plant where to it has been disposed. Furthermore the purified bacterial strain should be able to outcompete other microbes for resources in a plant growth medium. In addition, it is advisable that the purified bacterial strain not only reduce susceptibility to diseases but also effectively suppresses the growth of pathogens.

The present invention aims to resolve at least some of the disadvantages mentioned above. The aim of the invention is to provide means and methods to improve the growth and/or yield of an agricultural plant.

SUMMARY OF THE INVENTION

The applicants have identified novel bacterial strains as effective promotors of plant growth and/or yield, by improving a trait of agronomic importance on the one hand and conferring resistance to a plant pathogen infection on the other hand.

To this end, the present invention relates to a purified bacterial strain.

The current invention also relates to a bacterial population for improving plant growth and/or yield.

Furthermore, the invention relates to a microbial active ingredient for improving plant growth and/or yield.

The invention also relates to agricultural active formulations and a synthetic composition for improving plant growth and/or yield.

In another aspect, the present invention relates to improved plant growth and/or yield by improving a trait of agronomic importance. In another embodiment, the invention provides improved growth and/or yield of plants by effectively inhibiting the growth of a plant pathogen.

In yet another aspect, the invention relates to a method for conferring resistance to a plant pathogen infection in a plant.

In another aspect, the invention relates to methods for enhancing growth and/or yield of a plant by improving a trait of agronomic importance.

In a final aspect, the invention relates to a plant element.

DESCRIPTION OF FIGURES

The following description of the figures of specific embodiments of the invention is merely exemplary in nature and is not intended to limit the present teachings, their application or uses.

Per FIGS. 1 to 4 the graph on the left visualizes the estimates of the dry biomass with 95% confidence intervals for treated seeds and mock treated seeds, whereas the graph on the right visualizes the estimates of the difference between treated and mock treated seeds in dry biomass with its 95% confidence interval. The percentage indicates the difference in dry biomass expressed as a percentage of the mock treatment.

FIG. 1A-1E show a graphical representation of the increased dry biomass per plant at 6 weeks after sowing of wheat plants obtained from seeds treated with a formulation comprising a purified bacterial strain. Bacterial strains with Deposit ID B/00216, B/00215, B/00176 and B/00214 (FIG. 1A); B/00210 and B/00211 (FIG. 1B); B/00212 (FIG. 1C); B/00208, B/00210, and B/00181 (FIG. 1D); and B/00187 (FIG. 1E) demonstrate an increase in dry biomass per wheat plant.

DETAILED DESCRIPTION OF THE INVENTION

Definitions

Figure 1A:
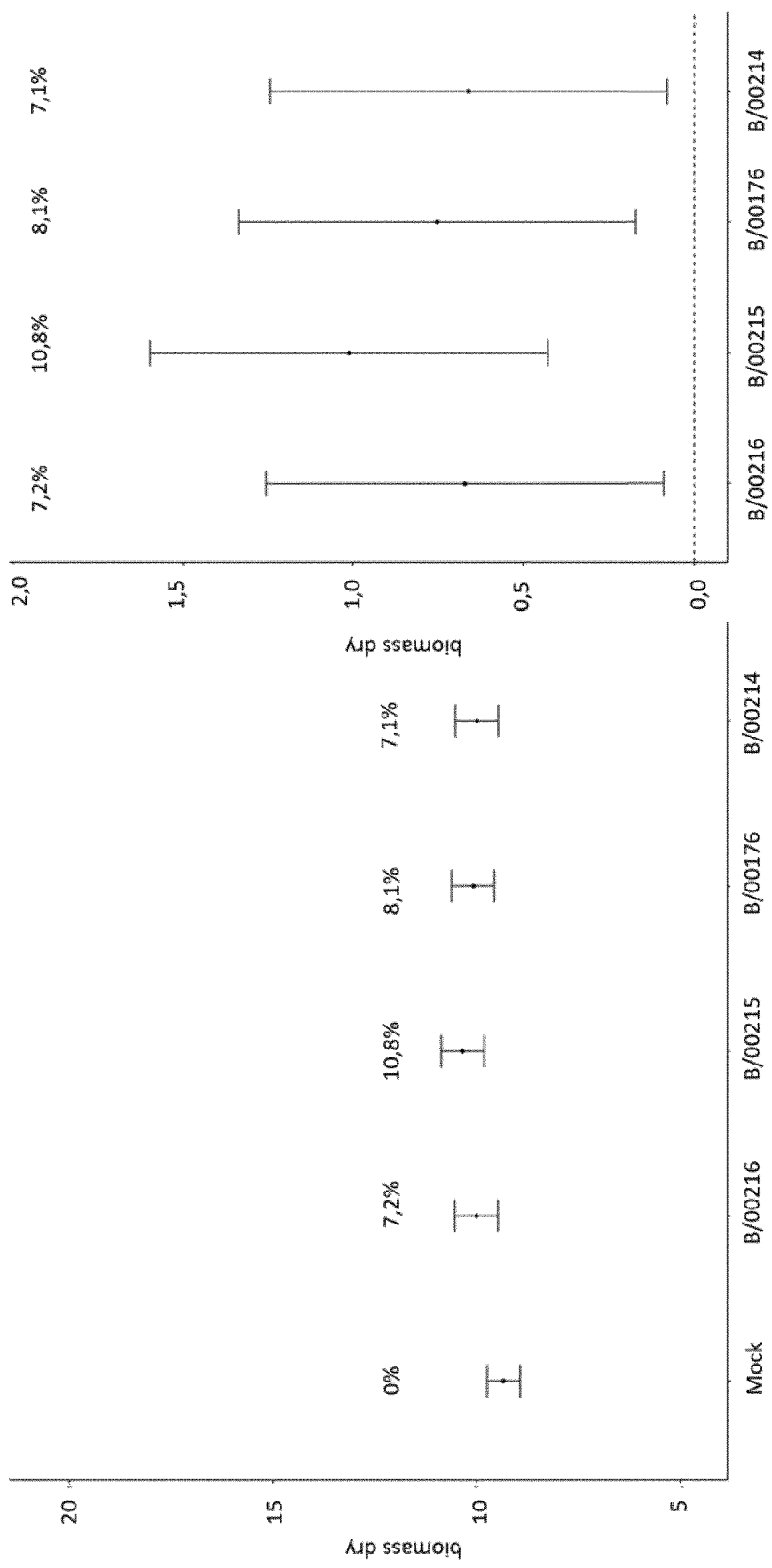
Figure 1B:
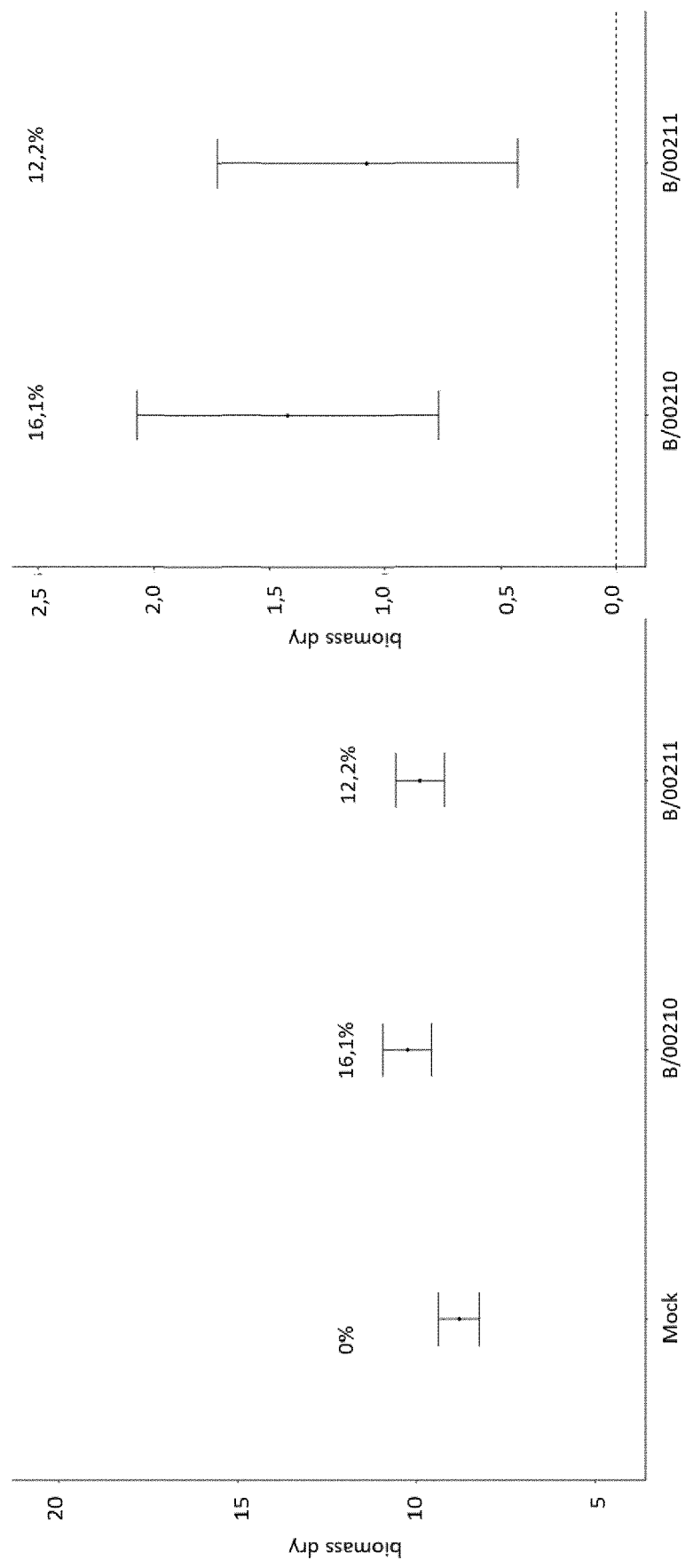
Figure 1D:
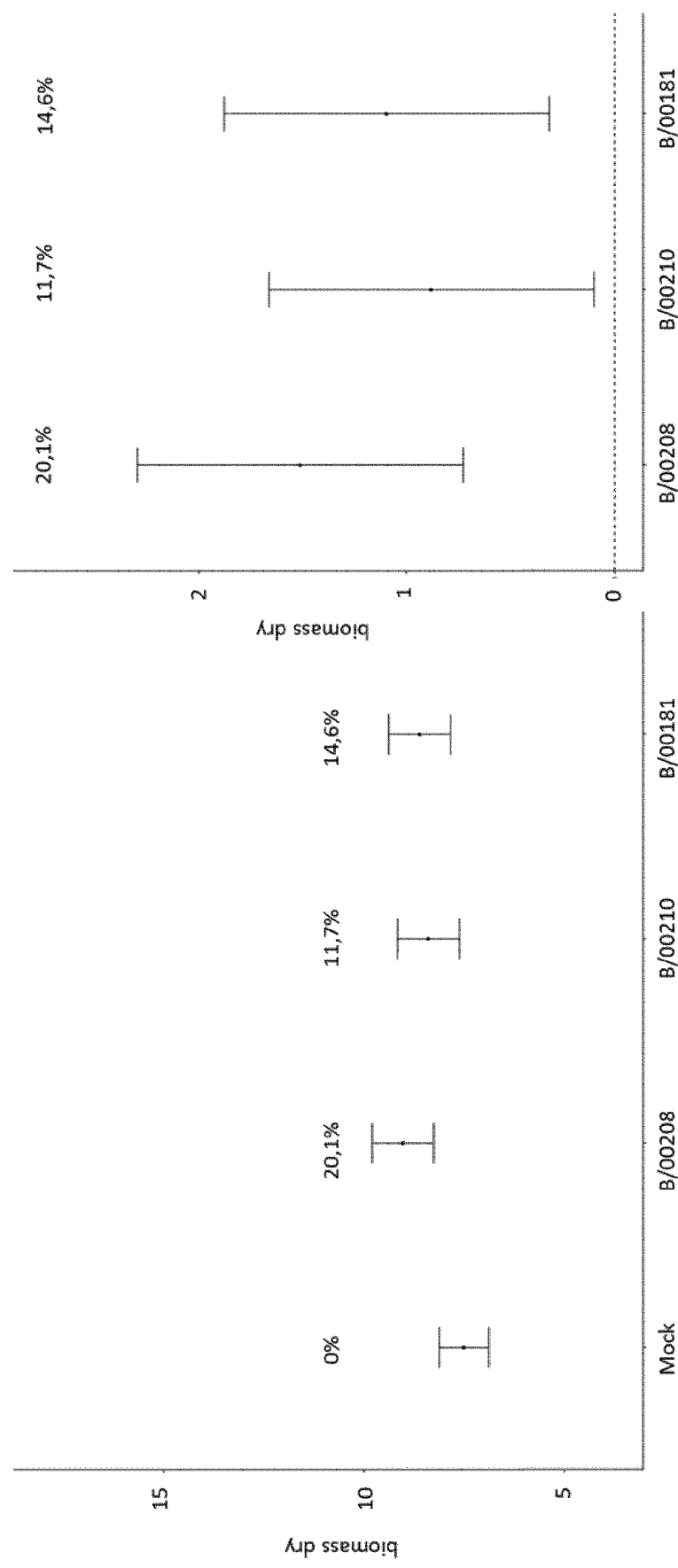
Figure 1E:
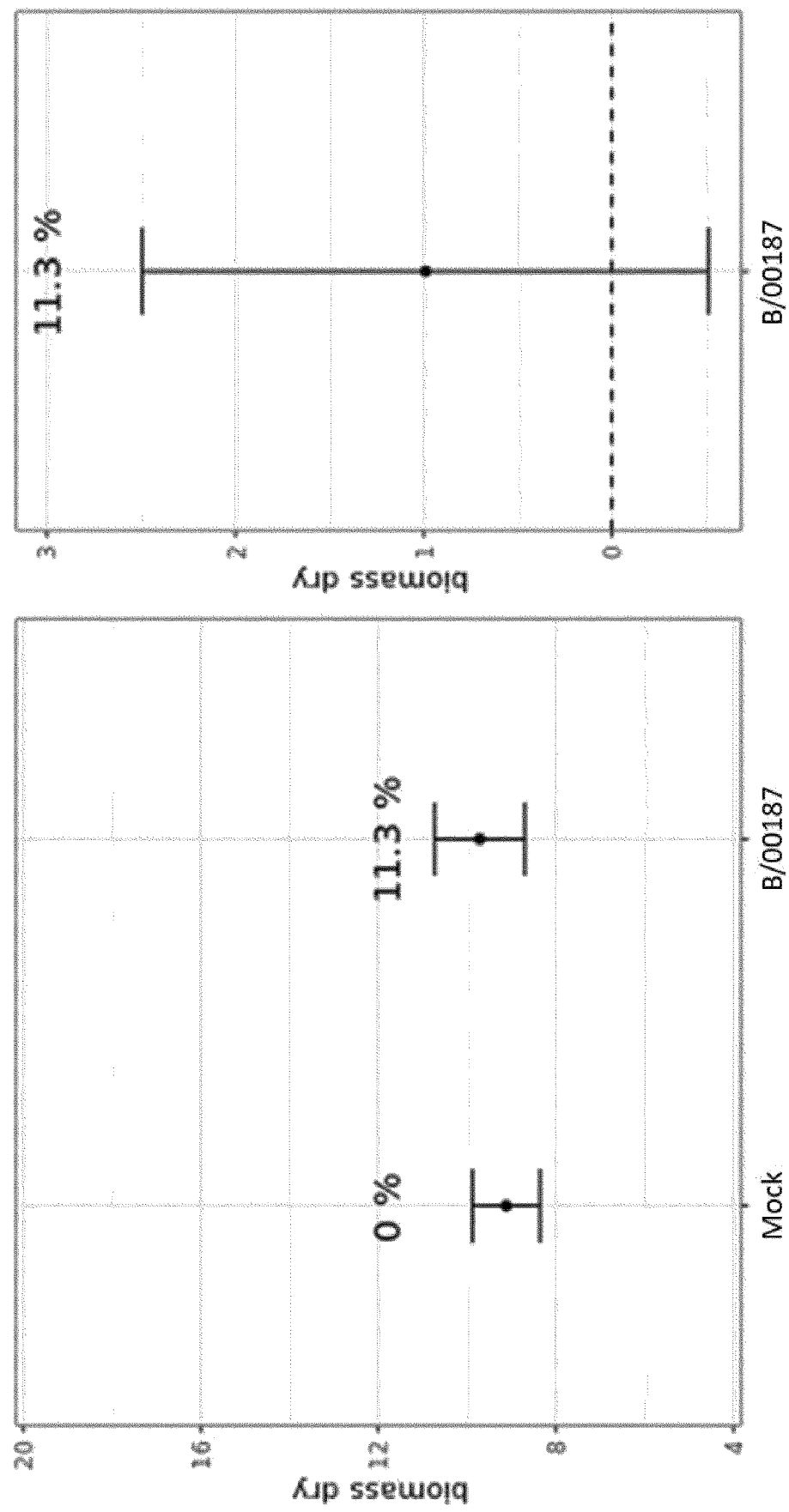

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

As used herein, "strain" or "bacterial strain" refers to any of the prokaryotic microorganism belonging to the same class of species, including the species. The purified bacterial strain of current invention may be an endophyte.

An "endophyte" is an organism capable of living on a plant element (e.g. rhizoplane or phyllosphere) or within a plant element (e.g. endosphere) or on a surface in close physical proximity with a plant element (e.g. the rhizosphere or on a seed). Endophytes can occupy the intracellular or extracellular spaces of plant tissue, including but not limited to leaves, stems, flowers, fruits, seeds, or roots. An endophyte can be, for example, a bacterial or fungal organism, and can confer a beneficial property to the host plant such as an increase in yield, biomass, resistance, or fitness. An endophyte can be a fungus or a bacterium. As used herein, the term "microbe" or "strain" is sometimes used to describe an endophyte. As used herein, the microbes or strains as described herein can be labelled as endophytes.

As used herein, the term "microorganism" or "microbe" refers to any species or taxon of microorganism, including, but not limited to, archaea, bacteria, microalgae, fungi (including mold and yeast species), mycoplasmas, microspores, nanobacteria, oomycetes, and protozoa. In some embodiments, a microbe or microorganism is a bacterial strain. In some embodiments, a microbe or microorganism is an endophyte, for example a bacterial or fungal endophyte, which is capable of living within a plant. In some embodiments, a microbe or microorganism encompasses individual cells (e.g., unicellular microorganisms) or more than one cell (e.g., multi-cellular microorganism).

As used herein, the term "bacterium", "bacteria", or "bacterial" refers in general to any prokaryotic organism, and may reference an organism from either Kingdom Eubacteria (Bacteria), Kingdom Archaebacteria (Archaea), or both. In some cases, bacterial genera have been reassigned due to various reasons (such as, but not limited to, the evolving field of whole genome sequencing), and it is understood that such nomenclature reassignments are within the scope of any claimed genus.

The term "16S nucleotide sequence" or "16S" refers to the DNA sequence of the 16S ribosomal RNA (rRNA) sequence of a bacterium. 16S rRNA gene sequencing is a well-established method for studying phylogeny and taxonomy of bacteria. A full length 16S nucleic acid sequence counts for approximately 1500 nucleotides in length.

"Biomass" means the total mass or weight (fresh or dry), at a given time, of a plant tissue, plant tissues, an entire plant, or population of plants. Biomass is usually given as weight per unit area. The term may also refer to all the plants or species in the community (community biomass).

The term "purified" is intended to specifically reference an organism, cell, tissue, polynucleotide, or polypeptide that is removed from its original source. The term "purified" does not necessarily reflect the extent to which the microbe has been purified.

As used herein, a "purified bacterial strain" is a strain that has been removed from its natural milieu. The term "purified bacterial strain" refers to substantially no other strains than the desired strain, and is therefore substantially free of other contaminants, which can include microbial contaminants. Further, as used herein, "purified bacterial strain" is intended to mean the strain separated from materials with which it is normally found in nature. A strain heterologous disposed to other strains, or with compounds or materials that it is not normally found with in nature, is still defined as "purified bacterial strain".

A "plant" or "host plant" includes any plant, particularly a plant of agronomic importance, within which or onto which a strain, is heterologous disposed. As used herein, a strain is said to colonize a plant, plant element, root or seed, when it can exist as a strain in relationship with a plant or plant element during at least part of either the plant's or the microbe's life cycle. In some embodiments, a strain is said to "colonize" a plant or plant element when it can be stably detected within the plant or plant element over a period time, such as one or more days, weeks, months or years. Some of the compositions and methods described herein involve a plurality of microbes in an amount effective to colonize a plant.

The terms "identity" or "identical" in the context of nucleotide sequences refer to the nucleotides in the two sequences that are the same when aligned for maximum correspondence. There are different algorithms known in the art that can be used to measure nucleotide sequence identity. Nucleotide sequence identity can be measured by a local or global alignment, preferably implementing an optimal local or optimal global alignment algorithm. For example, a global alignment may be generated using an implementation of the Needleman-Wunsch algorithm. For example, a local alignment may be generated using an implementation of the Smith-Waterman algorithm.

A gap is a region of an alignment wherein a sequence does not align to a position in the other sequence of the alignment. In global alignments, terminal gaps are discarded before identity is calculated. For both local and global alignments, internal gaps are counted as differences. A terminal gap is a region beginning at the end of a sequence in an alignment wherein the nucleotide in the terminal position of that sequence does not correspond to a nucleotide position in the other sequence of the alignment and extending for all contiguous positions in that sequence wherein the nucleotides of that sequence do not correspond to a nucleotide position in the other sequence of the alignment.

The term "reference plant" or "reference" is a comparative term, and references plants that are genetically identical, but may differ in treatment. In one example, two genetically identical maize plant embryos may be separated into two different groups, one receiving a treatment (such as transformation with a heterologous polynucleotide, to create a genetically modified plant) and one control, e.g., reference, that does not receive such treatment. Any phenotypic differences between the two groups may thus be attributed solely to the treatment and not to any inherency of the plant's genetic makeup. In another example, two genetically identical wheat seeds may be treated with a formulation, one that introduces an bacterial population and one that does not. Any phenotypic differences between the plants derived from (e.g., grown from or obtained from) those seeds may be attributed to the bacterial treatment.

Similarly, by the term "reference agricultural plant," it is meant an agricultural plant of the same species, variety, or cultivar to which a treatment, formulation, composition or bacterial strain preparation as described herein is not administered/contacted. A reference agricultural plant, therefore, is identical to the treated plant with the exception of the presence of the bacterial strain and can serve as a control for detecting the effects of the bacterial strain that is conferred to the plant.

A "reference environment" refers to the environment, treatment or condition of the plant in which a measurement is made. For example, production of a compound in a plant heterologous disposed to a bacterial strain can be measured in a reference environment of drought stress, and compared with the levels of the compound in a reference agricultural plant under the same conditions of drought stress. Alternatively, the levels of a compound in plant heterologous disposed to a bacterial strain and reference agricultural plant can be measured under identical conditions of no stress.

A "plant element" is intended to generically reference either a whole plant or a plant component, including but not limited to plant tissues, parts, and cell types. A plant element is preferably one of the following: whole plant, seedling, meristematic tissue, ground tissue, vascular tissue, dermal tissue, seed, leaf, root, shoot, stem, flower, ear, spike, spikelet, fruit, stolon, bulb, tuber, corm, keikis, bud. As used herein, a "plant element" is synonymous to a "portion" of a plant, and refers to any part of the plant, and can include distinct tissues and/or organs, and may be used interchangeably with the term "tissue" throughout. In addition, a "plant element" is intended to generically reference any part of a plant that is able to initiate other plants via either sexual or asexual reproduction of that plant, for example but not limited to: seed, seedling, root, shoot, cutting, scion, graft, stolon, bulb, tuber, corm, keikis, or bud.

"Agricultural plants" or "plants of agronomic importance" include plants that are cultivated by humans for food, feed, fiber, fuel, and/or industrial purposes. In some embodiments, plants (including seeds and other plant elements) treated in accordance with the present invention are monocots. In a particular embodiment, the agricultural plant is selected from the group consisting of wheat (*Triticum aestivum* and related varieties), barley (*Hordeum vulgare* and related varieties) or maize (*Zea mays* and related varieties).

An "active formulation" refers to a mixture of chemicals that facilitate the stability, storage, and/or application of the purified bacterial strain(s). Treatment formulations may comprise any one or more agents such as: a carrier, a solvent, an adjuvant, an oil, an emulsifier, a spreader, a cryoprotectant, a binder, a dispersant, a surfactant, a buffer, a tackifier, a microbial stabilizer, a fungicide, a complexing agent, an herbicide, a nematicide, an insecticide, a plant growth regulator, a rodenticide, a desiccant, a nutrient, an excipient, a wetting agent, or a salt.

As used herein an "agriculturally compatible carrier" refers to any material, other than water, that can be added to a plant element without causing or having an adverse effect on the plant element (e.g., reducing seed germination) or the plant that grows from the plant element, or the like.

As used herein, a "colony-forming unit" or "CFU" is used as a measure of viable microorganisms in a sample. A CFU is an individual viable cell capable of forming on a solid medium a visible colony whose individual cells are derived by cell division from one parental cell.

The term "supernatant" refers to the liquid broth remaining when cells grown in said broth are removed by centrifugation, filtration, sedimentation or other means well known in the art.

The term "extract" refers to various forms of microbial products. Said microbial products are obtained by removing the cell walls and/or cell membranes of the bacterial strains, a process known as lysis. Thereby obtaining one or more endogenous products of the bacterial strains in culture.

As used herein, a microbe, plant, or plant element is "modified" when it comprises an artificially introduced genetic or epigenetic "modification". In some embodiments, the modification is introduced by a genome engineering technology. In some embodiments, the modification is introduced by a targeted nuclease. In some embodiments, targeted nucleases include, but are not limited to, transcription activator-like effector nuclease (TALEN), zinc finger nuclease (ZNF), clustered regulatory interspaced short palindromic repeats (CRISPR), CRISPR/Cas9, CRISPR/CPFL and combinations thereof. In some embodiments, the modification is an epigenetic modification. In some embodiments, the modification is introduced by treatment with a DNA methyltransferase inhibitor such as 5-azacytidine, or a histone deacetylase inhibitor such as 2-amino-7-methoxy-3H-phenoxazin-3-one. In some embodiments, the modification is introduced via tissue culture. In some embodiments, a modified microbe, plant, or plant element comprises a transgene.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Diverse plant-associated microorganisms can positively impact plant health and physiology in a variety of ways. The bacterial strains described in the current invention provide several significant advantages to plants, in particular agricultural plants, like wheat, barley and maize.

In a first aspect the invention concerns a purified bacterial strain, wherein said strain is useful for improving plant growth and/or yield, wherein said bacterial strain comprises at least one 16S nucleotide sequence that is at least 95% identical to a sequence selected from the group consisting of SEQ ID NOs: 1 to 13 or as described in Table 1. Preferably, said strain has a 16S sequence at least 95% identical to a sequence selected from SEQ ID NOs: 1, 3, 4, 5, 6, 7, 8, or 13. Preferably, said purified bacterial strain comprises at least one 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 13 or as described in Table 1, more preferably according to SEQ ID NOs: 1, 3, 4, 5, 6, 7, 8, or 13.

In an embodiment of current invention, the purified bacterial strain comprises at least one 16S nucleotide sequence as described in Table 1. In other words, the purified bacterial strain comprises at least one 16S nucleotide sequence identical, i.e. 100%, to a 16S nucleotide sequence as described in Table 1. Preferably, said strains have a 16S sequence identical to a sequence selected from SEQ ID NOs: 1, 3, 4, 5, 6, 7, 8, or 13.

In another embodiment, the purified bacterial strain comprises one 16S nucleotide sequence that is at least 95% identical to at least one sequence selected from the group consisting of SEQ ID NOs: 1 to 13 or as described in Table 1, more preferably according to SEQ ID NOs: 1, 3, 4, 5, 6, 7, 8, or 13. In a further embodiment, said purified bacterial strain comprises one 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 13 or as described in Table 1, more preferably according to SEQ ID NOs: 1, 3, 4, 5, 6, 7, 8, or 13.

In another or further embodiment, the purified bacterial strain comprises two 16S nucleotide sequence copies that is at least 95% identical to at least one sequence selected from the group consisting of SEQ ID NOs: 1 to 13 or as described in Table 1, more preferably according to SEQ ID NOs: 1, 3, 4, 5, 6, 7, 8, or 13. According to a particular embodiment, said purified bacterial strain comprises two 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 13 or as described in Table 1, more preferably according to SEQ ID NOs: 1, 3, 4, 5, 6, 7, 8, or 13.

In another embodiment, the purified bacterial strain comprises at least two 16S nucleotide sequence copies that are at least 95% identical to at least two sequences selected from the group consisting of SEQ ID NOs: 1 to 13 or as described in Table 1, more preferably according to SEQ ID NOs: 1, 3, 4, 5, 6, 7, 8, or 13. In another or further embodiment, said purified bacterial strain comprises at least two 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 13 or as described in Table 1, more preferably according to SEQ ID NOs: 1, 3, 4, 5, 6, 7, 8, or 13.

According to another embodiment, the purified bacterial strain comprises at least three, preferably at least four, at least five, at least six, at least seven, at least eight, at least nine, at least ten, at least eleven, at least twelve, at least thirteen, at least fourteen, at least fifteen 16S nucleotide sequence copies that are at least 95% identical to at least two sequences selected from the group consisting of SEQ ID NOs: 1 to 13 or as described in Table 1, more preferably according to SEQ ID NOs: 1, 3, 4, 5, 6, 7, 8, or 13. In another or further embodiment, said purified bacterial strain comprises at least two 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 13 or as described in Table 1, more preferably according to SEQ ID NOs: 1, 3, 4, 5, 6, 7, 8, or 13.

According to another embodiment, the purified bacterial strain comprises multicopy 16S nucleotide sequence copies, that are at least 95% identical to at least two sequences selected from the group consisting of SEQ ID NOs: 1 to 13 or as described in Table 1, more preferably according to SEQ ID NOs: 1, 3, 4, 5, 6, 7, 8, or 13. In another or further embodiment, said purified bacterial strain comprises at least two 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 13 or as described in Table 1, more preferably according to SEQ ID NOs: 1, 3, 4, 5, 6, 7, 8, or 13.

In a preferred embodiment, the purified bacterial strain is useful for improving a trait of agronomic importance in a plant, wherein said bacterial strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13.

In a more preferred embodiment, the purified bacterial strain is useful for the plant to overcome stress conditions, such as nutrient stress, wherein said bacterial strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13.

In another embodiment, the purified bacterial strain is useful for conferring resistance to a plant pathogen infection in a plant, wherein said bacterial strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13.

In more preferred embodiment, the purified bacterial strain is useful for conferring resistance to a *Fusarium* infection in a plant, wherein said bacterial strain comprises at least one 16S nucleotide sequence at least 95% identical to at least one sequence selected from the group consisting of SEQ ID NOs: 1 or 11 or as described in Table 1, more preferably according to SEQ ID NOs: 1, 3, 4, 5, 6, 7, 8, or 13.

The purified bacterial strains of current invention are useful for conferring resistance to a plant pathogen infection in a plant, plant element and growth medium.

In a preferred embodiment, the purified bacterial strain is deposited with the Polish Collection of Microorganisms, under the terms of the Budapest Treaty respectively with Deposit ID: B/00215, B/00176, B/00214, B/00212, B/00210, B/00211, B/00216, B/00209, B/00208, B/00188, B/00181, B/00186, B/00187.

In an embodiment, the purified bacterial strain improves the plant growth and/or yield, and said strain is as deposited with Deposit ID: B/00215, B/00176, B/00214, B/00212, B/00210, B/00211, B/00216, B/00209, B/00208, B/00188, B/00181, B/00186, or B/00187. Preferably, said strain is as deposited with Deposit ID: B/00216, B/00215, B/00214, B/00212, B/00210, B/00211, B/00209, or B/00187.

In a further embodiment of current invention, the 16S nucleotide sequence identity is determined over a region of alignment of at least 100 nucleotides. In a preferred embodiment, the 16S nucleotide sequence identity is determined over a region of alignment of at least 100 nucleotides inclusive of any internal gaps.

In another embodiment, the 16S nucleotide sequence identity is determined over a region of alignment of at least 200 nucleotides, more preferably at least 300 nucleotides, more preferably at least 400 nucleotides, more preferably at least 500 nucleotides. In a preferred embodiment, the 16S nucleotide sequence identity is determined over a region of alignment of at least 200 nucleotides, preferably at least 300 nucleotides, preferably at least 400 nucleotides, more preferably at least 500 nucleotides inclusive of any internal gaps. In a more preferred embodiment the 16S nucleotide sequence identity is determined over a region of alignment considering a full length 16S sequence nucleotide.

In a second aspect the invention concerns a bacterial population comprising two or more purified bacterial strains, wherein said strains are described in the invention.

The bacterial population of current invention comprises two or more (e.g. 3, 4, 5, 6, 7, 8, 9, 10, 15, 20, 25 or greater than 25) purified bacterial strains, wherein said strains originate from different families of bacteria, or different genera of bacteria, or from the same genera but different species of bacteria. The taxonomic different bacterial strains can be obtained from the same cultivar of plant, different cultivars of the same plant, or different species of the same type of plant. The bacterial strains can be obtained from the soil wherein the plant is grown. In an embodiment in which two or more purified bacterial strains are used, each of the bacterial strains can have different properties or activities, e.g. produce different metabolites, produce different enzyme, confer different beneficial traits.

Preferably, the purified bacterial strains in said bacterial population are present in about equal amounts. Preferably, the concentration of each purified bacterial strain in said bacterial population is at least $10^2$ CFU/ml or spores/ml at least $10^2$ CFU/ml or spores/ml, at least $10^4$ CFU/ml or spores/ml, at least $10^5$ CFU/ml or spores/ml, at least $10^6$ CFU/ml or spores/ml, at least $10^7$ CFU/ml or spores/ml, at least $10^8$ CFU/ml or spores/ml, at least $10^9$ CFU/ml or spores/ml, or at least $10^{10}$ CFU/ml or spores/ml when said formulation is a liquid formulation. More preferably, the concentration of each purified bacterial strain in said bacterial population is between $10^3$ to $10^{10}$ CFU/ml or spores/ml, between $10^4$ to $10^{10}$ CFU/ml or spores/ml, between $10^5$ to $10^{10}$ CFU/ml or spores/ml, between $10^6$ to $10^{10}$ CFU/ml or spores/ml, between $10^6$ to $10^9$ CFU/ml or spores/ml, between $10^7$ to $10^9$ CFU/ml or spores/ml, or between $10^8$ to $10^9$ CFU/ml or spores/ml when said formulation is a liquid formulation. When said formulation is a non-liquid formulation, the concentration of each purified bacterial strain in said bacterial population is similar to the concentration in a liquid formulation, as mentioned above, but expressed as CFU/mg non-liquid formulation.

The purified bacterial strains described in current invention are capable of colonizing plants. Successful colonization can be confirmed by detecting the presence of the strain within the plant. For example, after applying the strain to the plant elements, high titers of the strain can be detected in the roots and shoots of the plants that germinate from said plant elements. Detecting the presence of the strain inside the plant can be accomplished by measuring the viability of the strain after surface sterilization of the plant element or the plant: strain colonization results in an internal localization of the strain, rendering it resistant to conditions of surface sterilization. The presence and quantity of strain can also be established using other means known in the art, for example, immunofluorescence microscopy using microbe-specific antibodies, or fluorescence in situ hybridization. Alternatively, specific nucleic acid probes recognizing conserved sequences from an strain can be employed to amplify a region, for example by quantitative PCR, and correlated to CFUs by means of a standard curve.

In some cases, the strains described herein are capable of moving from one tissue type to another. For example, the present invention's detection and isolation of strains within the mature tissues of plants after treating the exterior of a plant element demonstrates their ability to move from the plant element into the vegetative tissues of a maturing plant. Therefore, in some embodiments, the population of bacterial strains is capable of moving from the plant element exterior into the vegetative tissues of a plant. In some embodiments, the strain that is disposed onto the plant element of a plant is capable, upon germination of the plant element into a vegetative state, of localizing to a different tissue of the plant. For example, strains can be capable of localizing to any one of the tissues in the plant, including: the root, adventitious root, seminal root, root hair, shoot, leaf, flower, ear, spike, spikelet, bud, tassel, meristem, pollen, pistil, ovaries, stamen, fruit, stolon, rhizome, nodule, tuber, trichome, guard cells, hydathode, petal, sepal, glume, rachis, vascular cambium, phloem, and xylem. In an embodiment, the strain is capable of localizing to the root and/or the root hair of the plant. In another embodiment, the strain is capable of localizing to the photosynthetic tissues, for example, leaves and shoots of the plant. In other cases, the strain is localized to the vascular tissues of the plant, for example, in the xylem and phloem. In still another embodiment, the strain is capable of localizing to the reproductive tissues (flower, pollen, pistil, ovaries, stamen, fruit, spike, spikelet) of the plant. In another embodiment, the strain is capable of localizing to the root, shoots, leaves and reproductive tissues of the plant. In still another embodiment, the strain colonizes a fruit or plant element tissue of the plant. In still another embodiment, the strain is able to colonize the plant such that it is present in the surface of the plant (i.e. its presence is detectably present on the plant exterior). In still other embodiments, the strain is capable of localizing to substantially all, or all, tissues of the plant. In some cases, strains are capable of replicating within the host plant and colonizing the plant.

In one embodiment, the purified bacterial strain or bacterial population can be cultured on a culture medium or can be adapted to culture on the culture medium. Said culture medium is sterile prior to being inoculated with said bacterial strain and comprises all nutrients for growth and maintenance of the strain on the culture medium. In addition, the culture medium can be in a solid, semi-solid or liquid form.

In a following aspect, current invention concerns a microbial active ingredient for improving plant growth and/or yield, wherein said ingredient comprises one or more substances isolated from a culture wherein the purified bacterial strain of current invention or the bacterial population of current invention is incubated.

Preferably the microbial active ingredient comprises one or more substances isolated from a bacterial culture comprising one or more bacterial strains or bacterial population of current invention.

Bacterial strains produce a plethora of small compounds and secondary metabolites that can be secreted in the culture or be stored endogenously. Therefore, in a particular embodiment, a supernatant from the culture wherein the bacterial strain or bacterial population of current invention has been cultured is useful for improving plant growth and/or yield. In another embodiment, an extract or extract fraction from the culture wherein the bacterial strain or bacterial population of current invention has been cultured is useful for improving plant growth and/or yield. Non-limiting examples of endogenous products are amino acids, peptides, enzymes, secondary metabolites, vitamins, minerals. Removing the cell walls and/or cell membranes of the bacterial strains in culture can be obtained by several procedures which are well-known by the person skilled in the art. Non-limiting examples are the addition of chemicals to said culture, heating said culture or induce lysis in a mechanical way. An extract can also be obtained by autolysis of the bacterial strains.

In a preferred embodiment, the microbial active ingredient comprises a spore suspension, spray dried spores, or whole cell broth.

To administer the purified bacterial strain or bacterial population to plants, plant elements or growth media, it is advisable to formulate the strains in a formulation or composition, wherein said formulation or composition may also comprise other biologicals or agrochemicals to simulate plant growth.

In certain embodiments, the strain is selected on the basis of its compatibility with commonly used biologicals or agrochemicals. Plants, particularly agricultural plants, can be treated with a vast array of biologicals or agrochemicals.

In some cases, it can be important for the strain to be compatible with biologicals or agrochemicals, particularly those with complexing properties, in order to persist in the plant although, there are many such complexing agents that do not penetrate the plant, at least at a concentration sufficient to interfere with the strain. Therefore, where a systemic complexing agent is used in the plant, compatibility of the strain to be inoculated with such agents will be an important criterion. In an embodiment, purified bacterial strains that are compatible with biologicals or agrochemicals can be used to inoculate plants, plant elements or growth media according to the methods described herein.

Bactericide-compatible strain can also be isolated by selection on liquid medium. The culture of strains can be plated on petri dishes without any forms of mutagenesis; alternatively, strains can be mutagenized using any means known in the art. For example, strain cultures can be exposed to UV light, gamma-irradiation, or chemical mutagens such as ethylmethanesulfonate (EMS), ethidium bromide (EtBr) dichlovos (DDVP, methyl methane sulphonale (MMS), triethylphosphate (TEP), trimethylphosphate (TMP), nitrous acid, or DNA base analogs, prior to selection on fungicide comprising media. Finally, where the mechanism of action of a particular bactericide is known, the target gene can be specifically mutated (either by gene deletion, gene replacement, site-directed mutagenesis, etc.) to generate a strain that is resilient against that particular chemical. It is noted that the above-described methods can be used to isolate strains that are compatible with both bacteriostatic and bactericidal compounds.

The biological or agrochemical compatible strains generated can be detected in samples. For example, where a transgene was introduced to render the strain compatible with the biological(s) or agrochemical(s), the transgene can be used as a target gene for amplification and detection by PCR. In addition, where point mutations or deletions to a portion of a specific gene or a number of genes results in compatibility with the biological(s) or agrochemical(s), the unique point mutations can likewise be detected by PCR or other means known in the art. Such methods allow the detection of the strain even if it is no longer viable.

Furthermore, the invention concerns an agricultural active formulation comprising an agriculturally compatible carrier and one or more bacterial strains or a bacterial population at a concentration of at least about $10^2$ CFU/ml or spores/ml in a liquid formulation or about $10^2$ CFU/mg in a non-liquid formulation, wherein said bacterial strain and bacterial population are described herein.

Preferably, said agriculturally compatible carrier may be a natural or synthetic organic or inorganic material with which the bacterial strains or products derived from the culture of said bacterial strains are combined to facilitate their application into the plant element, plant or plant growth medium. Furthermore, said carrier is generally inert and must be acceptable for use in agriculture. One of ordinary skill in the art can readily determine the appropriate carrier to be used.

Non-limiting examples of said agricultural active formulation are soluble powders, soluble granules, wettable granules, tablet formulations, dry flowables, aqueous flowables, wettable dispersible granules, oil dispersions, suspension concentrates, dispersible concentrates, emulsifiable concentrates, aqueous suspensions, a fertilizer granule, or a sprayable.

In a preferred embodiment said agricultural active formulation comprises at least one oil, surfactant and polymer. Preferably, said formulation further comprises one or more of the following: fungicide, nematicide, bactericide, insecticide, molluscicide, algicide, herbicide, fertilizer, micronutrient fertilizer material, stabilizer, preservative, carrier, complexing agent, or any combination thereof. In a preferred embodiment, the bacterial strain and bacterial population of the formulation are shelf-stable, and said formulation is shelf-stable. Optionally, the shelf-stable formulation is in a dry formulation, a powder formulation, or a lyophilized formulation. In some embodiments, the formulation is formulated to provide stability for the strains. In one embodiment, the formulation is substantially stable at temperatures between about −20° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the formulation is substantially stable at temperatures between about 4° C. and about 37° C. for at least about 5, 10, 15, 20, 25, 30 or greater than 30 days.

In another embodiment, an agricultural active formulation comprises an agriculturally compatible carrier and one or more microbial active ingredients at a concentration of at least about 10^2 CFU/ml or spores/ml in a liquid formulation or about 10^2 CFU/mg in a non-liquid formulation, wherein the microbial active ingredient is described in current invention. Preferably, the concentration of one or more microbial active ingredients is effective to improve the plant growth and/or yield.

In a preferred embodiment, any of the bacterial strains of current invention is heterologous disposed to the plant element in the agricultural active formulation. In another preferred embodiment, any of the bacterial populations of current invention is heterologous disposed to the plant element in the agricultural active formulation. In another and further embodiment, any of the microbial active ingredients of current invention is heterologous disposed to the plant element in the agricultural active formulation. In addition to the plant element, the plant itself or the growth medium wherein the plant or plant element is grown can be treated with any of the bacterial strains, bacterial populations, microbial active ingredients or agricultural active formulations of current invention.

In another aspect, the invention provides a synthetic composition comprising a plant element and a heterologous disposed bacterial strain or bacterial population to said plant element, wherein the bacterial strain or bacterial population is described in current invention, and wherein the synthetic composition is capable of improving plant growth and/or yield as compared to a reference plant element not further comprising the strain or bacterial population.

In a preferred embodiment, the synthetic composition comprises the plant element and a heterologous disposed bacterial population to said plant element. In a more preferred embodiment, the synthetic composition comprises the plant element and a heterologous disposed microbial active ingredient to said plant element.

In another embodiment, any of the synthetic compositions described herein are shelf-stable. The bacterial strain may be shelf-stable, where at least 0.01%, of the CFUs are viable after storage in desiccated form (i.e. moisture content of 30% or less) for 1, 2, 3, 4, 5, 6, 7, 8, 9, 10 or greater than 10 weeks at 4° C. or at room temperature. Optionally, a shelf-stable composition is in a dry composition, a powder composition, or a lyophilized composition. In some embodiments, the composition is formulated to provide stability for the strains. In an embodiment, the composition is substantially stable at temperatures between about −20° C. and about 50° C. for at least about 1, 2, 3, 4, 5, or 6 days, or 1, 2, 3 or 4 weeks, or 1, 2, 3, 4, 5, 6, 7, 8, 9, 10, 11 or 12 months, or one or more years. In another embodiment, the composition is substantially stable at temperatures between about 4° C. and about 37° C. for at least about 5, 10, 15, 20, 25, 30 or greater than 30 days. Preferably the composition is substantially stable at temperatures between about 4° C. and about 37° C. for at least one year or greater than one year.

In a further embodiment, any of the synthetic compositions described herein further comprise a plant element, wherein said plant element is a seed, optionally wherein the seed is modified. Preferably, the plant element is placed into a substrate that promotes plant growth, optionally soil. In a particular embodiment, a plurality of said plant elements are placed in the soil in rows, with substantially equal spacing between each seed within each row.

In another or further embodiment, any of the synthetic compositions described herein further comprise one or more of the following: stabilizer, preservative, carrier, surfactant, complexing agent, or any combination thereof and/or one or more of the following: fungicide, nematicide, bactericide, insecticide, or herbicide.

In a preferred embodiment, any of the synthetic compositions described herein are confined within an object selected from the group consisting of: bottle, jar, ampule, package, vessel, bag, box, bin, envelope, carton, container, silo, shipping container, truck bed, or case.

In a preferred embodiment related to the aspect, current invention concerns a plant grown from the synthetic composition as described in previous embodiments, wherein said plant exhibits a trait of agronomic interest, selected from the group consisting of disease resistance, drought tolerance, heat tolerance, cold tolerance, salinity tolerance, metal tolerance, herbicide tolerance, chemical tolerance, improved water use efficiency, improved phosphorus solubilization, improved phosphorus mobilization, improved nitrogen utilization, improved nitrogen fixation, pest resistance, herbivore resistance, pathogen resistance, increase in yield, increase in yield under water-limited conditions, health enhancement, vigor improvement, growth improvement, improved plant emergence, photosynthetic capability improvement, nutrition enhancement, altered protein content, altered oil content, increase in biomass, increase in number of tillers per plant, increase in shoot length, increase in root length, improved root architecture, increase in seed weight, altered seed carbohydrate composition, altered seed oil composition, increase in radical length, delayed senescence, stay-green, altered seed protein composition, increase in dry weight of mature plant reproductive elements, increase in fresh weight of mature plant reproductive elements, increase in number of mature plant reproductive elements per plant, increase in chlorophyll content, reduced number of wilted leaves per plant, reduced number of severely wilted leaves per plant, increase in number of non-wilted leaves per plant, or improved plant visual appearance.

In some embodiments, the invention uses microbes that are heterologous to a plant or plant element in making a microbial active ingredient, an agricultural active formulation or a synthetic composition. A microbe is considered heterologous to the plant, plant element or plant growth medium if the plant, plant element or plant growth medium is untreated (e.g., a seed that is not treated with a bacterial strain described herein) does not contain detectable levels of the microbe. A microbe is considered "heterologous disposed" on the exterior surface of or within a plant or plant tissue when the microbe is applied or disposed on the plant in a number that is not found on that plant before application of the microbe. For example, a purified bacterial strain disposed on an exterior surface or within the seed can be an endophytic bacterium that may be associated with the mature plant, but is not found on the surface of or within the seed. As such, a microbe is deemed heterologous disposed when applied on the plant that either does not naturally have the microbe on its surface or within the particular tissue to which the microbe is disposed, or does not naturally have the microbe on its surface or within the particular tissue in the number that is being applied.

In another embodiment, the strain is heterologous disposed, for example, on the surface of a reproductive element of a plant, in an amount effective to be detectable in the mature a plant. In a particular embodiment, the strain is heterologous disposed in an amount effective to be detectable in an amount of at least about 100 CFU between 100 and 200 CFU, at least about 200 CFU, between 200 and 300 CFU, at least about 300 CFU, between 300 and 400 CFU, at least about 500 CFU, between 500 and 1,000 CFU, at least about 1,000 CFU, between 1,000 and 3,000 CFU, at least about 3,000 CFU, between 3,000 and 10,000 CFU, at least about 10,000 CFU, between 10,000 and 30,000 CFU, at least about 30,000 CFU, between 30,000 and 100,000 CFU, at least about 100,000 CFU or more in the mature plant.

In yet another aspect, current invention concerns the bacterial strain, the bacterial population, the microbial active ingredient, the agricultural active formulation, or the synthetic composition as described above for use in improving plant growth and/or yield by improving a trait of agronomic importance in a plant.

Said bacterial strain is capable of increasing nutrient uptake and/or nutrient use efficiency of a treated plant as compared to a reference plant. Furthermore said bacterial strain is capable of increasing the nitrogen fixating capacities or phosphorus uptake of a treated plant as compared to a reference plant. In particular, said bacterial strain is capable of increasing the amount of biomass of a treated plant as compared to a reference plant. Preferably, said bacterial strain is capable of increasing the number of tillers per plant of a treated plant as compared to a reference plant. Preferably, these improved traits of agronomic importance result in an increased growth of plants, more specifically in an increased yield.

For example, the purified bacterial strain may provide an improved trait of agronomic importance in a plant that is of at least 3%, between 3% and 5%, at least 5%, between 5% and 10%, least 10%, between 10% and 15%, for example at least 15%, between 15% and 20%, at least 20%, between 20% and 30%, at least 30%, between 30% and 40%, at least 40%, between 40% and 50%, at least 50%, between 50% and 60%, at least 60%, between 60% and 75%, at least 75%, between 75% and 100%, at least 100%, between 100% and 150%, at least 150%, between 150% and 200%, at least 200%, between 200% and 300%, at least 300% or more, when compared with the reference plants grown under the same conditions.

The bacterial population and microbial active ingredient of current invention improve the same traits of agronomic importance in a plant as described above.

An aspect of current invention also concerns the bacterial strain, the bacterial population, the microbial active ingredient, agricultural active formulation, or the synthetic composition as earlier described for use in improving plant growth and/or yield by effectively inhibiting the growth of a plant pathogen, preferably a plant pathogen of the genus *Fusarium*.

Said use of bacterial strains, bacterial populations, microbial active ingredients, agricultural active formulations, or synthetic compositions for conferring resistance to a plant pathogen infection is an efficient and ecological application of biocontrol.

*Fusarium* is a large genus of filamentous fungi, widely distributed in soil and associated with plants. Some *Fusarium* spp. produce mycotoxins in cereal crops and can affect human and animal health if they enter the food chain.

It is contemplated that methods may be used to improve plant growth and/or yield by improving a characteristic of agronomic importance to a plant and/or by conferring resistance to a plant pathogen infection in a plant.

The methods described herein can also be used with transgenic plants comprising one or more exogenous transgenes, for example, to yield additional trait benefits conferred by the newly introduced bacterial strain(s).

In another aspect, current invention concerns a method for conferring resistance to a plant pathogen infection in a plant, by means of treating said plant with a purified bacterial strain, a bacterial population, a microbial active ingredient or an agriculturally active formulation, wherein said strain, population, ingredient, or formulation are described in current invention.

In another embodiment related to the aspect, current invention also provides a method for conferring resistance to a plant pathogen infection in a plant element by means of treating said plant element with the strain, population, ingredient, or formulation as described herein.

In a further embodiment, the invention provides a method for conferring resistance to a plant pathogen infection in a plant by means of treating the plant and/or a plant and/or growth medium wherein said plant is grown, with the strain, population, ingredient, or formulation are described herein. In another embodiment related to the aspect, current invention also provides a method for conferring resistance to a plant pathogen infection in a plant element by means of treating the plant element and/or the plant growth medium wherein said plant element is cultured with the strain, population, ingredient, or formulation as described herein. Preferably, the method for conferring resistance to a *Fusarium* infection in a plant is provided by means of treating (e.g. spraying) plant ears with the strain, population, ingredient, or formulation described herein. Preferably, a wheat ear, spike, spikelet, stem and/or leave is treated with the strain, population, ingredient, or formulation of current invention to confer resistance to a *Fusarium* infection. More preferably, the strain, population, ingredient, or formulation with Deposit ID B/00188 and/or B/00181 are used in a method for conferring resistance to a *Fusarium* infection. Optionally, one may treat the plant growth medium (e.g. soil) with the strain, population, ingredient, or formulation as described herein for conferring resistance to a soil borne plant pathogen.

Treatment of the plant element, plant or plant growth medium with the purified bacterial strain, bacterial population, microbial active ingredient, agriculturally active formulation confers resistance to a plant pathogen infection. Furthermore, said treatment effectively inhibits growth of the plant pathogen in the plant element, plant or plant growth medium, wherein said plant element, plant or plant growth medium is infected with the plant pathogen.

As a result plant pathogen infection can be prevented in treated agricultural plants. And if agricultural plants are infected with the plant pathogen, in case said plant was not treated against the plant pathogen or was wrongly treated against the plant pathogen, the treatment results in an growth inhibition of the plant pathogen. Despite the pathogen infection, the plant growth and/or yield can improve.

In a following aspect, the current invention concerns a method of improving plant growth and/or yield, comprising the step of treating a plant element with a purified bacterial strain, a bacterial population, or a microbial active ingredient in an amount effective to increase the growth and/or yield in the plant derived from the treated plant element relative to a plant derived from a reference plant element, wherein said purified bacterial strain comprises at least one 16S nucleotide sequence at least 95% identical to a sequence selected from the group consisting of SEQ ID NOs: 1 to 13 or as described in Table 1, more preferably according to SEQ ID NOs: 1, 3, 4, 5, 6, 7, 8, or 13, said bacterial population comprises two or more of said strains, and said microbial active ingredient comprises one or more substances isolated from a culture wherein said bacterial strain or said bacterial population is incubated.

Preferably said purified bacterial strain comprises at least one 16S nucleotide sequence that is between 95% and 96%, at least 96%, between 96% and 97%, at least 97%, between 97% and 98%, at least 98%, between 98% and 99%, at least 99%, at least 99.1%, at least 99.2%, at least 99.3%, at least 99.4%, at least 99.5%, at least 99.6%, at least 99.7%, at least 99.8%, at least 99.9% identical to a sequence selected from the group consisting of SEQ ID NOs: 1 to 13 or as described in Table 1, more preferably according to SEQ ID NOs: 1, 3, 4, 5, 6, 7, 8, or 13.

As used herein, a purified bacterial strain is considered to have conferred an improved agricultural trait whether or not the improved trait arose from the plant, the strain, or the concerted action between the plant and bacterial strain. Therefore, for example, whether a beneficial hormone or chemical is produced by the plant or the strain, for purposes, the strain will be considered to have conferred an improved agronomic trait upon the host plant, as compared to a reference plant that has not been heterologous disposed to said strain.

In a preferred embodiment, the purified bacterial strain is heterologous disposed to a plant element in an amount effective to increase a trait of agronomic importance in the plant derived from the treated plant element relative to a plant derived from a reference plant element, wherein said purified bacterial strain is described in current invention. In a preferred embodiment, the amount of the heterologous disposed strain to the plant element is effective to maintain a critical population mass in said plant element. In a further embodiment, the amount of the heterologous disposed strain to the plant element is effective to maintain a critical population mass in the mature plant germinated from said plant element.

In a more preferred embodiment, the bacterial population, the microbial active ingredient, the agricultural active formulation, or the synthetic composition is heterologous disposed to a plant element in an amount effective to increase a trait of agronomic importance in the plant derived from the treated plant element relative to a plant derived from a reference plant element, wherein said population, ingredient, formulation or composition are described in current invention.

In one embodiment, said plant element is modified. A person skilled in the art is familiar with a variety of conventional and more advanced methods to modify plant elements. According to another embodiment the plant element is any plant element with the intrinsic characteristics of plant propagation. Because of the totipotency of plants, any part of the plant may be used (e.g. a stem cutting, a leaf section, a portion of a root), though it is usually a highly meristematic part such as root and stem ends, buds, tubers, bulbs, rhizome, stolon or any plant part for vegetative reproduction. In sexual reproduction, a plant element is a seed or spore. According to a preferred embodiment the plant element is a portion of the root or a seed. Preferably, a wheat ear, spike, spikelet, stem and/or leave is modified.

In some embodiments, plant elements of the present invention include wild plants and domesticated varieties. Plant elements may be developed by any technique, including but not limited to directed evolution, selection, marker assisted selection, hybridization, outcrossing, backcrossing, in-breeding, polyploidization, reverse breeding, doubled haploids, induced mutation, other genetic or epigenetic modifications, and combinations thereof.

In one embodiment, it is contemplated that the plant, more in particular the agricultural plant, of the present invention is wheat (*Triticum aestivum* and related varieties), barley (*Hordeum vulgare* and related varieties) or maize (*Zea mays* and related varieties).

In another aspect, the current invention concerns a method of improving plant growth and/or yield, comprising the step of treating a plant element with a first purified bacterial strain and a second purified bacterial strain in an amount effective to increase growth and/or yield in the plant derived from the treated plant element relative to a plant derived from a reference plant element, characterized in that, said first strain comprises at least one 16S nucleotide sequence at least 95% identical to a sequence selected from the group consisting of SEQ ID NOs 1 to 13 or as described in Table 1, more preferably according to SEQ ID NOs: 1, 3, 4, 5, 6, 7, 8, or 13; and said second strain comprises at least one 16S nucleotide sequence at least 95% identical to a sequence selected from the group consisting of SEQ ID NOs 1 to 13 or as described in Table 1, more preferably according to SEQ ID NOs: 1, 3, 4, 5, 6, 7, 8, or 13.

Said first and second purified bacterial strain are described in current invention as purified bacterial strains. In one embodiment related to the aspect the first and second bacterial strain are two taxonomic identical bacterial strains. In particular, said strains originate from the same families, genera, or species of bacteria. Said strains may differ on the strain level. Optionally, the first and second bacterial strain related to the aspect are two taxonomic different bacterial strains. In particular, said strains originate from different families of bacteria, or different genera of bacteria, or from the same genera but different species of bacteria. The taxonomic different bacterial strains can be obtained from the same cultivar of plant, different cultivars of the same plant, or different species of the same type of plant. In embodiments in which two bacterial strains are used, each of the bacterial strains can have different properties or activities, e.g., produce different metabolites, produce different enzyme, confer different beneficial traits, show synergistic effects.

In another embodiment an additional, a third, purified bacterial strain is heterologous disposed to a plant element in an amount effective to improve growth and/or yield in the plant derived from the treated plant element relative to a plant derived from a reference plant element. Preferably, the plant element is treated with two or more purified bacterial strains in an amount effective to increase growth and/or yield in the plant derived from the treated plant element relative to a plant derived from a reference plant element. In particular, the plant element is treated with a bacterial population in an amount effective to increase growth and/or yield in the plant derived from the treated plant element relative to a plant derived from a reference plant element. In another or further embodiment, two or more purified bacterial strains are heterologous disposed to a plant element in an amount effective to inhibit the growth of the plant pathogen of the genus *Fusarium* on the plant grown from the treated plant element.

Current invention also discloses a method of improving plant growth and/or yield, comprising the steps of inoculating a plant growth medium with a purified bacterial strain, a bacterial population, or a microbial active ingredient; and growing a plant in said medium, wherein said strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13, said bacterial population comprises two or more of said strains, and said microbial active ingredient comprises one or more substances isolated from a culture wherein said bacterial strain or said bacterial population is incubated.

Inoculating a plant growth medium can be performed, by way of example and without the intention to be limiting, using a liquid, a powder, a granule, a pellet. Plants, in particular agricultural plants, can be grown in plant growth medium. In one embodiment, said plant growth medium is soil, sand, gravel, polysaccharide, mulch, compost, peat moss, straw, logs, clay, or a combination thereof. In another embodiment, the plant growth medium can also include a hydroculture system or an in vitro culture system.

In a particular embodiment, the method is provided for improving growth and/or yield of a plant, wherein said plant is free of disease and/or pathogen pressure and/or pest organisms. In a preferred embodiment, the method is provided to inhibit the growth of the plant pathogen.

Hydroculture is the growing of plants in a soilless medium or an aquatic based environment, while in vitro culture system refers to the growing of plants or explants on or in a recipient with synthetic medium, in sterile conditions, in a controlled environment and in reduced space. Explants refer to parts of a plant, from all the aerial part to isolated cells, as parts of leaves, of roots, seeds, bulbs, tubers, buds. The inoculation of said plant growth medium with, the purified bacterial strain, the bacterial population or the microbial active ingredient can be done before, during and/or after sowing or before, during and/or after the start of the plant growth cycle in case of hydroculture or in vitro culture. The inoculation can be performed once or multiple times during the plant growth cycle.

In a following aspect, the invention provides a method for improving plant growth and/or yield by artificially inoculating the plant with one or more purified bacterial strains, wherein said strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13, and wherein said strains are applied to said plant as a powder, pellet, granule or liquid.

In a preferred embodiment current invention provides a method for improving plant growth and/or yield by artificially inoculating said plant with the bacterial population, the microbial active ingredient, or the agriculturally active formulation as described in current invention.

In another embodiment the invention provides a method for enhancing plant growth and/or plant yield of a plant by artificially inoculating a plant element, in particular the root, of said plant with one or more purified bacterial strains, wherein said strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13, and wherein said strains are applied to said plant as a powder, pellet, granule or liquid.

In a more preferred embodiment of the invention, the method for enhancing plant growth and/or yield of the plant by artificially inoculating said plant with one or more purified bacterial strains, the bacterial population, the microbial active ingredient, or the agriculturally active formulation, wherein said strain, population, ingredient, or formulation are applied in an amount effective to increase the biomass and/or yield of the fruit or seed produced by the plant by at least 1%, at least 2%, at least 3%, at least 5%, at least 10%, at least 15%, at least 20%, at least 30%, at least 40%, at least 50%, at least 60%, at least 70%, at least 80%, at least 90%, at least 100%, or more, when compared with the fruit or seed of a reference agricultural plant.

In another aspect, the invention concerns a method of treating seeds of a plant to improve plant growth and/or yield, comprising mechanically or manually inoculating a plurality of plant seeds with an agricultural active formulation comprising an agriculturally acceptable carrier and a purified bacterial strain, wherein said strain comprises at least one 16S nucleotide sequence that is at least 95% identical to a 16S nucleotide sequence selected from the group consisting of SEQ ID NOs: 1 to 13 or as described in Table 1, more preferably according to SEQ ID NOs: 1, 3, 4, 5, 6, 7, 8, or 13, wherein the seed is inoculated with said strain in an amount effective to colonize a plant germinated from the inoculated seed and to increase the seed yield of a plant germinated from the inoculated seed as compared to a plant germinated from a reference seed grown and sowed under the same conditions.

In another embodiment, the method concerns inoculating the seeds of a plant with an agricultural active formulation, wherein said formulation comprises an agriculturally acceptable carrier and the purified bacterial strain, the bacterial population, or the microbial active ingredient of current invention.

In a preferred embodiment related to the aspect, the seed is coated with the bacterial strain, cultured with the bacterial strain or planted near the bacterial strain such that the strain is able to colonize the seed.

A further aspect of current invention also concerns a plant element, such as a seed, coated with the agricultural active formulation according to current invention. Also the purified bacterial strains or microbial consortia may be applied on a plant element as a coating.

Current invention also concerns a method for preparing a synthetic composition, wherein said method comprises the step of treating a plant element with a bacterial strain, wherein said strain comprises at least one 16S nucleotide sequence that is at least 95% identical to a 16S nucleic acid sequence selected from the group consisting of SEQ ID NOs: 1 to 13 or as described in Table 1, more preferably according to SEQ ID NOs: 1, 3, 4, 5, 6, 7, 8, or 13, wherein the bacterial strain is present in the composition in an amount capable of modulating at least one trait of agronomic importance in a plant selected from the group consisting of transcription of a gene, level of a transcript, the expression of a protein, level of a hormone, level of a metabolite, and population of endogenous microbes; in plants grown from said plant elements, as compared to reference plants grown from plant elements not treated with said composition.

A preferred embodiment of current invention concerns a method for preparing a synthetic composition, wherein said method comprises the steps of treating a plant element with the bacterial strain, the bacterial population, or the microbial active ingredient, wherein said strain, population and ingredient are described herein.

In a preferred embodiment of the method for preparing a synthetic composition, the bacterial strain is present in an amount of at least about $10^2$ CFU per plant element. In a more preferred embodiment of the method for preparing a synthetic composition, the bacterial strain is present in an amount of at least about $10^2$ per plant grown from the plant element.

Preferably the bacterial strain is present on the plant element in an amount effective to be detectable within a target tissue of the mature plant selected from a fruit, a seed, a leaf, or a root, or portion thereof. For example, the bacterial strain can be detected in an amount of at least about 100 CFU or spores, between 100 and 200 CFU or spores, at least about 200 CFU or spores, between 200 and 300 CFU or spores, at least about 300 CFU or spores, between 300 and 400 CFU or spores, at least about 500 CFU or spores, between 500 and 1,000 CFU or spores, at least about 1,000 CFU or spores, between 1,000 and 3,000 CFU or spores, at least about 3,000 CFU or spores, between 3,000 and 10,000 CFU or spores, at least about 10,000 CFU or spores, between 10,000 and 30,000 CFU or spores, at least about 30,000 CFU or spores, between 30,000 and 100,000 CFU or spores, at least about $10^5$ CFU or spores, between $10^5$ and $10^6$ CFU or spores at least about $10^6$ CFU or spores or more in the mature plant.

In a final aspect of current invention, the invention concerns a method of improving the efficacy of a purified bacterial strain in an application, comprising the selection of an additional purified bacterial strain, wherein said strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13, and wherein said additional strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13.

In a preferred embodiment of the method of improving the efficacy, the application is selected from the group consisting of: agriculture, plant improvement, water quality improvement, bioremediation, industrial compound production, pharmaceutical compound production, and production of bioengineered substances. In particular, the application is a production method of a composition belonging to a class of compound selected from the group consisting of: acids, alcohols, amino acids, amylases, antibiotics, biogases, bioplastics, citric acid, enzymes, esters, fatty acids, flavoring agents, glutamic acid, human or animal hormones, human growth hormone, ice, insulin, lactic acid, lipases, lipids, minerals, nitrogen, oils, nucleic acids, pectinases, preservatives, proteins, snow, sugars, vaccines, viruses, vitamins, and waxes.

Furthermore current invention concerns a method of improving the performance of a purified bacterial strain in an application, comprising the selection of an additional purified bacterial strain, wherein said strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13, and wherein said additional strain comprises at least one 16S nucleotide sequence at least 95% identical to at least one sequence selected from the group consisting of SEQ ID NOs: 1 to 13 or as described in Table 1, more preferably according to SEQ ID NOs: 1, 3, 4, 5, 6, 7, 8, or 13.

In some embodiments, the additional bacterial strain is associated with a plant element, and/or the bacterial strain is Gram-negative, and/or the bacterial strain is Gram-positive, and/or the bacterial strain has improved sporulation capability, and/or the bacterial strain comprises a characteristic selected from the group consisting of: efficacy, survivability, shelf-stability, tolerance to an antibiotic, tolerance to reduced environmental moisture.

The invention is further described by the following non-limiting examples which further illustrate the invention, and are not intended to, nor should they be interpreted to, limit the scope of the invention.

EXAMPLES

The present invention will now be further exemplified with reference to the following example(s). The present invention is in no way limited to the given examples or to the embodiments presented in the figures.

Example 1: Increased Dry Biomass and Increased Number of Tillers Per Plant in Wheat Per treatment, 5×24 wheat seeds are treated with a formulation containing a bacterial strain. Five planter boxes are filled with potting soil mix and saturated with water. As a control, 10×24 wheat seeds are treated with a formulation without bacterial strain to compare (mock treatment). Seeds are sown in three rows of 8 seeds per planter box. Nutrients are being added to the planter boxes at two and three weeks after sowing. The number of tillers per plant are counted at 6 weeks after sowing the wheat plants obtained from seeds treated with said the bacterial strain. After counting the number of tiller per plant, all shoots are cut off and fresh biomass is weighed per planter box (i.e. all 24 shoots together). Plant shoots are then dried at 60° C. for 1 week and dry biomass (in mg) is determined per planter box.

Figure 2A:
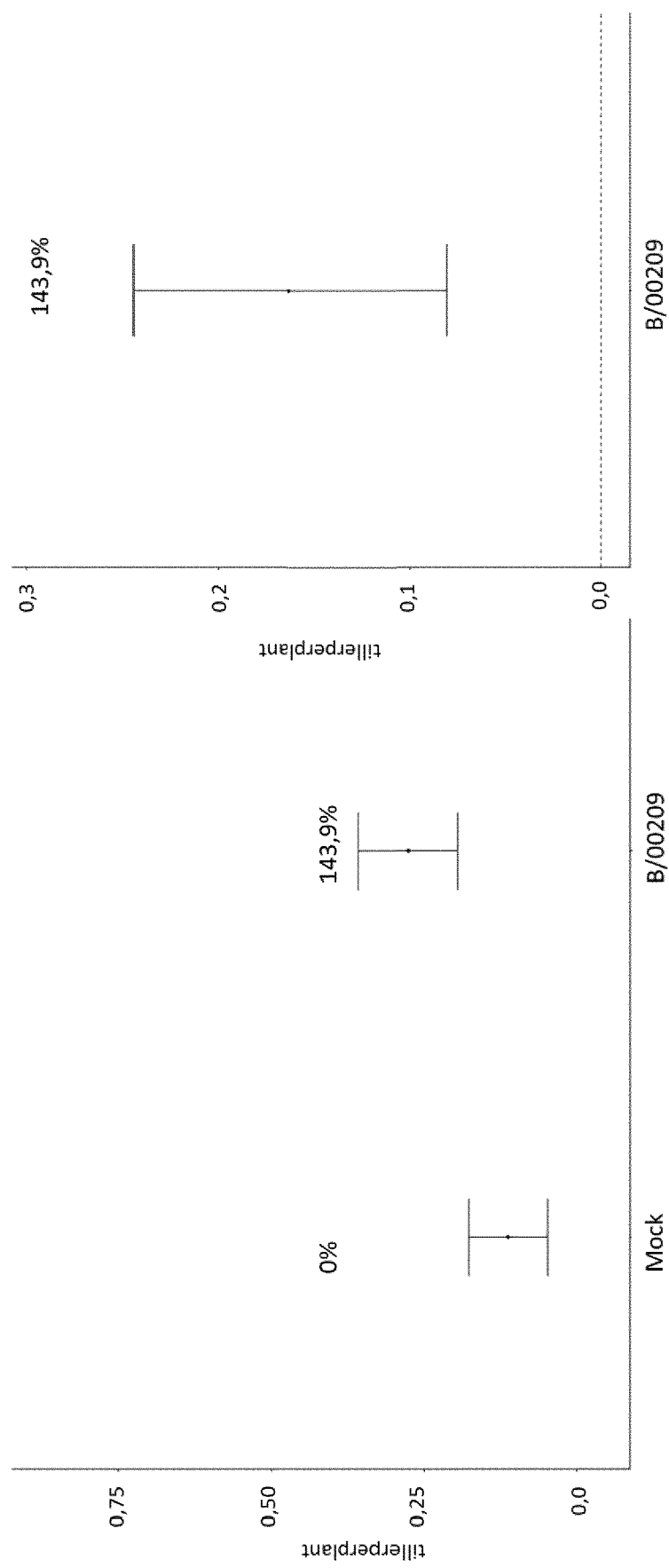
FIG. 2A-2C show a graphical representation of the increased number of tillers per wheat plant at 6 weeks after sowing of wheat plants obtained from seeds treated with a formulation comprising a purified bacterial strain. Bacterial strains with Deposit ID B/00209 (FIG. 2A); B/00208, B/00188, and B/00181 (FIG. 2B); and B/00186 (FIG. 2C) demonstrate an increase in the number of tillers per wheat plant.
Figure 2B:
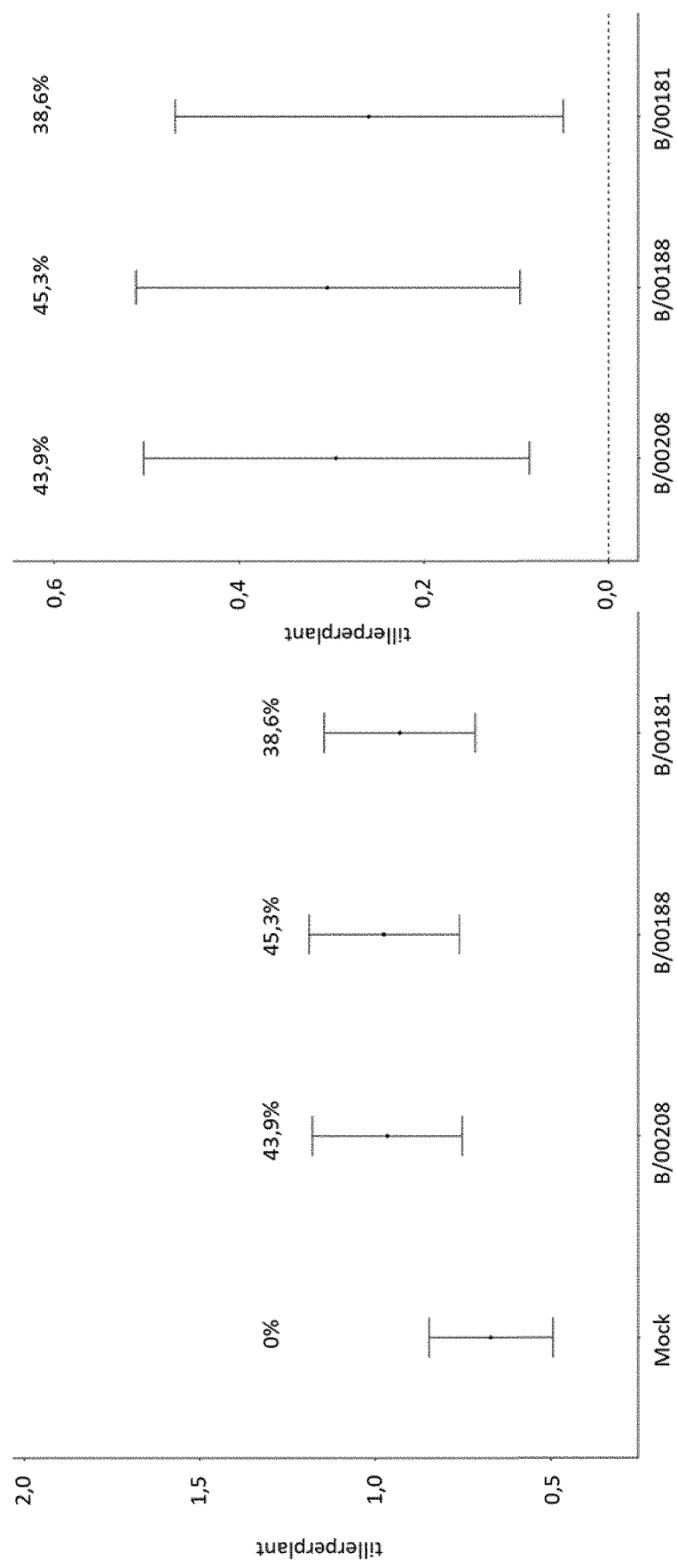
Figure 2C:
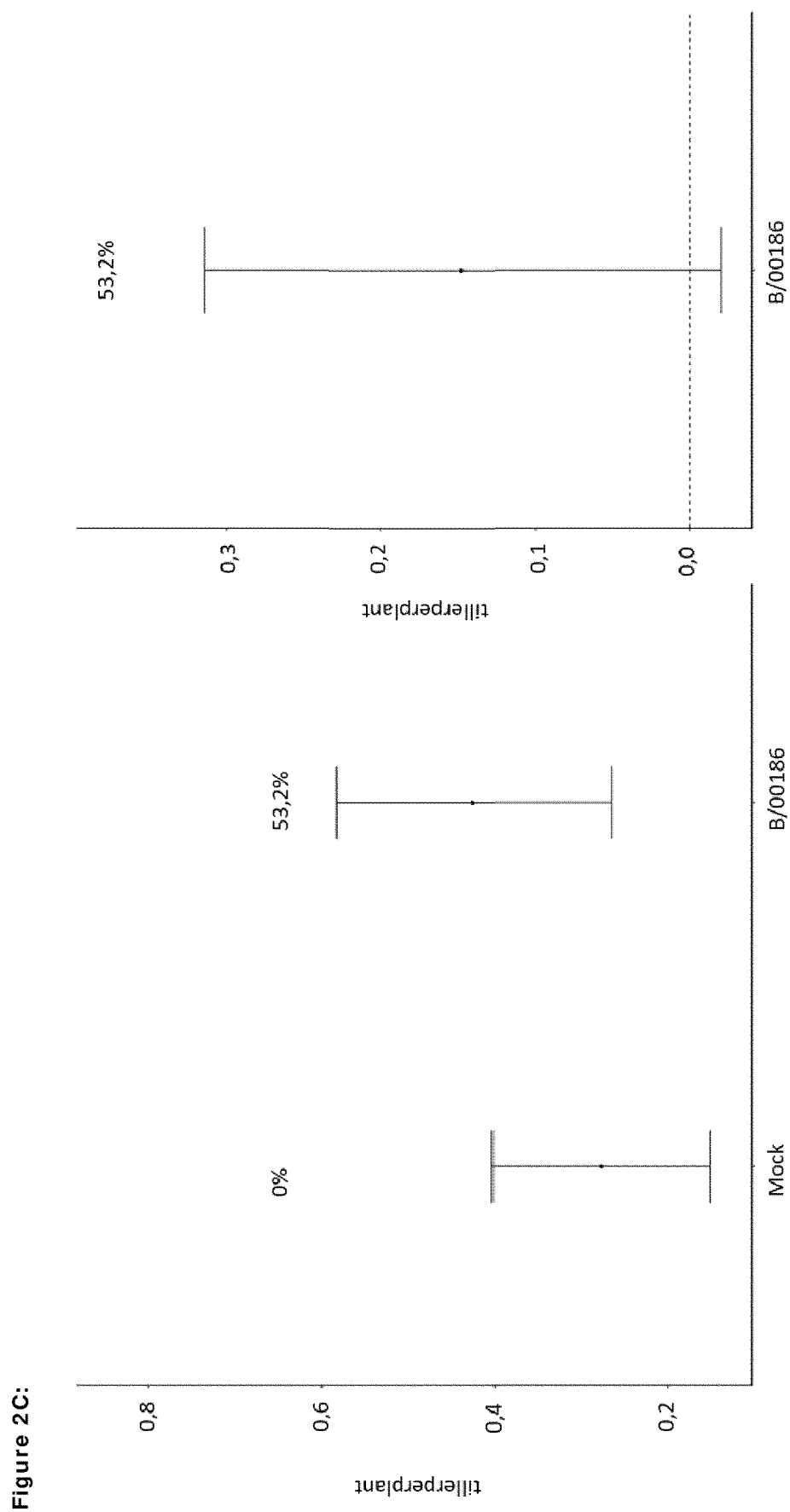

For all evaluated formulations, each containing a bacterial strain of current invention, an increase in dry biomass and/or an increase in number of tillers per plant is seen in reference to a formulation without bacterial strain. The increase in dry biomass ranges between 7.1% and 20.1% for the evaluated formulations, as visualized in FIGS. 1A-1E. The increase in number of tillers is visualized in FIGS. 2A-2C, and ranges between 38.6% and 143.9%.

Example 2: Increased Dry Biomass Per Plant in Wheat

Figure 3:
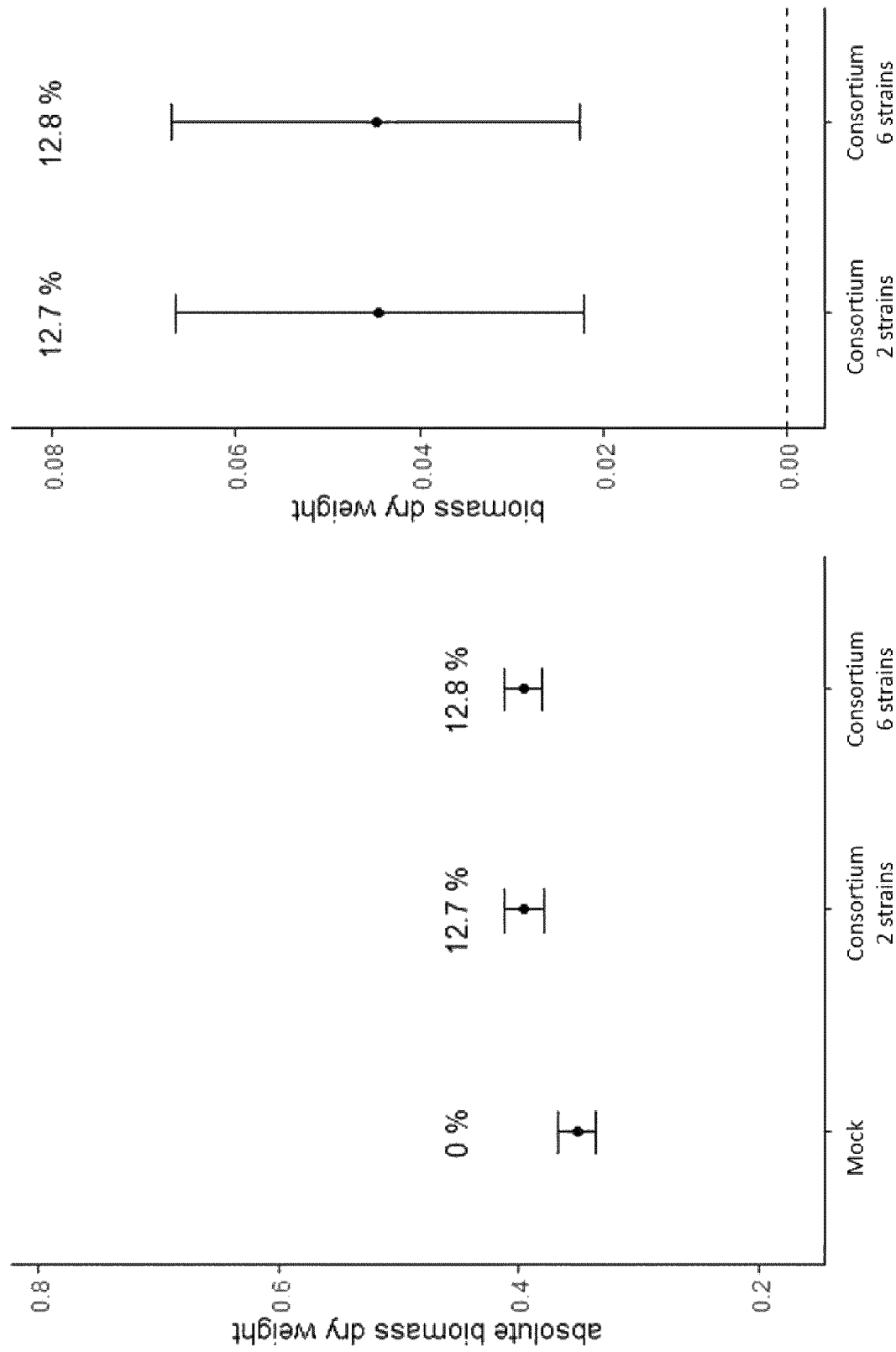
FIG. 3 shows a graphical representation of the increased dry biomass per wheat plant at 6 weeks after sowing of wheat plants obtained from seeds treated with a formulation comprising two bacterial strains, indicated on the graph with 'Consortium 2 strains', and from seeds treated with a formulation comprising six bacterial strains, indicated on the graph with 'Consortium 6 strains'. The two combined bacterial strains with Deposit ID B/00212 and B/00215 demonstrate an increase in dry biomass per wheat plant. Even the combination of six bacterial strains with Deposit ID B/00187, B/00211, B/00212, B/00214, B/00215, and B/00208.

Per treatment, 5×24 wheat seeds are treated with a formulation comprising two or six bacterial strains of current invention. Five planter boxes are filled with potting soil mix and saturated with water. As a control, 10×24 wheat seeds are treated with a formulation without bacterial strain to compare (mock treatment). Seeds are sown in three rows of 8 seeds per planter box. Nutrients are being added to the planter boxes at two and three weeks after sowing. Plant height of the middle row is measured 5 weeks after sowing. Six weeks after sowing, all shoots are cut off and fresh biomass is weighed per planter box (i.e. all 24 shoots together). Plant shoots are then dried at 60° C. for 1 week and dry biomass (in mg) is determined per planter box. A combination of two bacterial strains of current invention demonstrate an increase of 12.7% dry biomass (in mg) in reference to the mock (FIG. 3). A combination of six bacterial strains of current invention demonstrate an increase of 12.8% dry biomass (in mg) in reference to the mock (FIG. 3). The combination of bacterial strains establishes a synergistic effect, increasing the dry biomass of treated wheat.

Example 3: Increased Dry Biomass Per Plant in Maize

Figure 4:
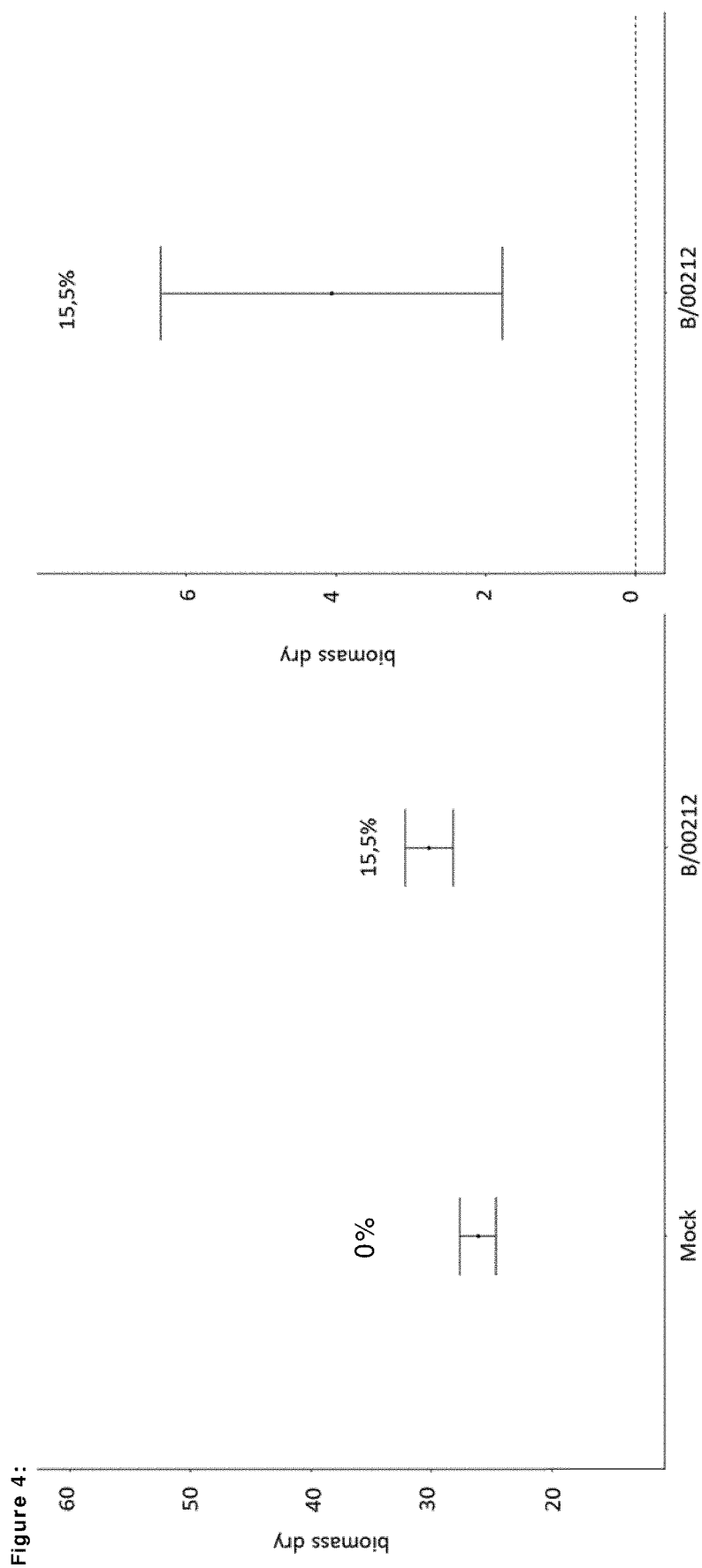
FIG. 4 shows a graphical representation of the increased dry biomass per maize plant at 6 weeks after sowing of maize plants obtained from seeds treated with a whole cell broth culture of a bacterial strain, a member of genus *Modestobacter*, with Deposit ID B/00212.

Per treatment, 5×24 maize seeds are treated with a whole cell broth wherein a purified bacterial strain a member of genus *Modestobacter* with Deposit ID B/00212 was incubated. Five planter boxes are filled with potting soil mix and saturated with water. As a control, 10×24 maize seeds are treated with a formulation without bacterial strain to compare (mock treatment). Seeds are sown in three rows of 8 seeds per planter box. Nutrients are being added to the planter boxes at two and three weeks after sowing. Plant height of the middle row is measured 5 weeks after sowing. Six weeks after sowing, all shoots are cut off and fresh biomass is weighed per planter box (i.e. all 24 shoots together). Plant shoots are then dried at 60° C. for 1 week and dry biomass (in mg) is determined per planter box. Maize plants treated with a whole cell broth wherein B/00212 was incubated show a 15.5% increase of dry biomass in reference to maize plants treated with a mock (FIG. 4).

Example 4: Growth Inhibition of the Plant Pathogen of Genus *Fusarium*

A co-culturing experiment of a purified bacterial strain member of the genus *Micromonospora* with Deposit ID B/00188 is executed with the fungal pathogen *Fusarium*, which is known to be a pathogen of many agricultural plants. Solid NA medium is prepared and dispensed over petri dishes with a diameter of 8 cm. The purified bacterial strain is cultured in a liquid Luria broth culture until a dense bacterial culture. An amount, in particular 10 µl, of the liquid culture is taken and inoculated at 2.5 cm from the center of the petri dish. The petri dish is incubated at 28° C. overnight. Thereafter, the center of the petri dish was inoculated with 15 µl of a liquid culture incubated with *Fusarium* (i.e. fungal plug) and incubated at 21° C. for at least three days. The petri dish is scored with score A, B, C or no effect depending on the fungal growth, wherein score A is given when fungal growth is limited to 1 cm from the fungal plug, score B is given when fungal growth is observed up to 2 cm from the fungal plug, score C is given when the fungal pathogen reaches the bacterial growth line, and no effect is scored when the fungal pathogen outcompetes the bacterial growth. The bacterial strain with Deposit ID B/00188 effectively inhibits the growth of *Fusarium* and is given a score A, as *Fusarium* growth is restricted to the fungal plug.

Example 5: Increased Grain Yield in Wheat in the Field

Figure 5:
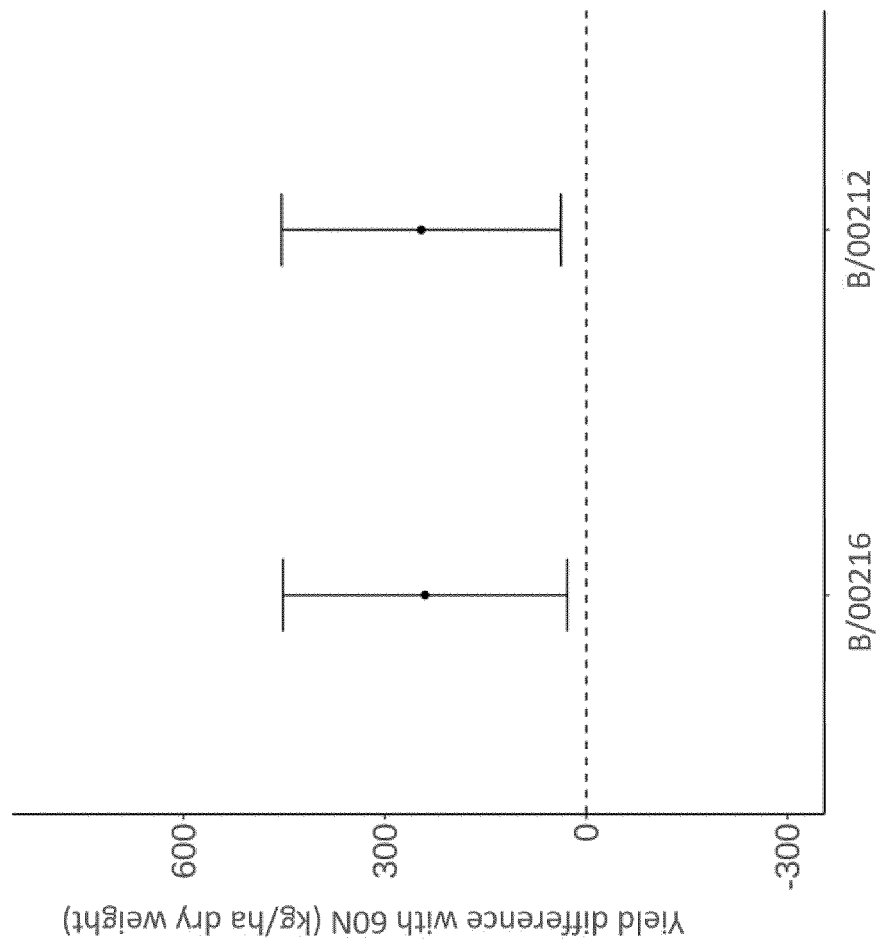
FIG. 5 shows a graphical representation of the increased seed yield. The wheat plants are obtained from wheat seeds treated with a formulation comprising a purified bacterial strain with Deposit ID B/00212 or B/00216.

Per treatment, 1.5 kg spring wheat seeds are coated with a formulation containing a purified bacterial strain and a colorant. The concentration of the purified bacterial strain in said formulation is between 10^4 to 10^6 CFU/ml. Seeds are sown on 4 replicate plots (15 m$^2$ plot size) per field location using standard agricultural practices. Sowing density is 400 seeds m$^2$. Sowing was done around April 5$^{th}$ and harvest happened around August 15$^{th}$. Fertilization was calculated based on soil analysis. 50 kg of phosphorus ($P_2O_5$) and 50 kg of potassium ($K_2O$) fertilizers were applied at sowing time. Nitrogen fertilizer was applied at two moments: 35 kg ha$^{-1}$ of at tillering stage and 55 kg ha$^{-1}$ at plant heading. Harvest was done with the Delta plot combine (Wintersteiger AG, Ried, Austria) and grain yield (kg/ha) was calculated based on the grain yield harvested at each individual plot and considering a seed moisture of 15%. Grain yield was compared with a mock treatment. Mock treated seeds are seeds coated with the same formulation and colorant but without a bacterial strain. The results of the treatment are visualized in FIG. 5. The graphs visualize the estimates of the grain yield with 95% confidence intervals for coated seeds and mock coated seeds. The dashed line in the graphs represents the mock treatment. Wheats treated with the formulation containing the purified bacterial strain B/00216 and colorant showed an increased yield of 4.5%. Also wheats treated with the formulation containing the purified bacterial strain B/00212 and colorant showed an increased yield of 4.4%. The purified bacterial strains B/00216 and B/00212 improve the plant yield.

Also for wheat seeds treated with a formulation, as indicated above, containing one of the purified bacterial strains B/00215, B/00214, B/00210, B/00211, B/00209, or B/00187, first results show that the yield of the wheat plants is greater than the mock treated seeds. An increased yield of about 5% is observed, which is in line with the results of the treatments with B/00216 an B/00212. (data not shown)

Sequence Deposit

The bacterial strains of current invention are were deposited on Jan. 18, 2019 with the Polish Collection of Microorganisms, Institute of Immunology and Experimental Therapy, Polish Academy of Sciences, Ul. Weigla 12, 53-114 Wroclaw, Poland, under the terms of the Budapest Treaty, with Deposit ID: B/00215, B/00176, B/00214, B/00212, B/00210, B/00211, B/00216, B/00209, B/00208, B/00188, B/00181, B/00186, and B/00187.

TABLE 1

SEQUENCE LISTING

Current application contains a Sequence Listing with 13 sequences and which are hereby incorporated by reference in its entirety. The 13 sequences are listed in Table 1. The full-length 16S nucleotide sequences of the purified bacterial strains of current invention are listed below and marked with a SEQ ID NO. Also the Deposit ID of each purified bacterial strain is noted in Table 1 with its corresponding 16S nucleotide sequence.

| Deposit ID | SEQ ID No | Organism (Genus species) | 16S nucleotide sequence (5'-3') |
|---|---|---|---|
| B/00215 | 1 | Modestobacter marinus | GACGAACGCTGGCGGCGTGCTTAACACATGCAAGTCGAGCGAGGCCCATCCTTCGGGTGGTGCCCTAG<br>CGGCCAACGGGTGAGTAACACGTGGGCAACCTGCCCTCCAGCTCTGGGATAACTCCAAGAAATTGTGCTA<br>ATACCGGATGTGACCGCTGACCGCATGGTCTGGTGGTGGAAAGATTCATCGGCTGAGGATGGGCCCGCG<br>GCCTATCAGCTTGTTGGTGGGGTAGTGGCCCACCAAGGCGACGACGGGTAGCCGGCCTGAGAGGTGAC<br>CGGCCACACTGGGACTGAGACACGGCCCAGACTCCTACGGGAGGCAGCAGTGGGGAATATTGCCAATG<br>GGCGGAAGCCTGACCCAGCCACGCCGCGTGAGGGATGACGGCCTTCGGGTTGTAAACCTCTTTCAGTAG<br>GGACGAAGCGAGAGTGACGGTACCTACAGAAGAAGCACCGGCTAACTACGTGCCAGCAGCCGCGGTAAT<br>ACGTAGGGTGCAAGCGTTGTCCGGAATTATTGGGCGTAAAGAGCTCGTAGGCGGTCTGTCGCGTCGGCT<br>GTGAAAACCCGAGGCTCAACCTCGGGCCTGCAGTCGATACGGGCAGACTAGAGTACTCGAGGGAGACT<br>GGAATTCCTGGTGTAGCGGTGAAATGCGCAGATATCAGGAGGAACACCGGTGGCGAAGGCGGGTCTCTG<br>GGCAGTAACTGACCGCTGAGGAGCGAAAGCGTGGGGAGCGAACAGGATTAGATACCCTGGTAGTCCACGC<br>CGTAAACGTTGGGCGCTAGGTGTGGGGCAACAGCTAAAACTCAAAGGAATTGACGGGGCCCGCACAAGCGGCGG<br>CCCGGCTGGAGTACGGCCGCAAGGCTAAAACTCAAAGGAATTGACGGGGCCCACAAGCGGCGG<br>AGCATGTGGTTTAATTCGATGCAACGCGAAGAACCTTACCTAGGCTTGACATGCACGGAAATCTGTAGAG<br>ATACGGGGTGCCTTTGGCCGTGCACAGGTGGTGCATGGTTGTCGTCAGCTCGTGTCGTGAGATGTTGG<br>GTTAAGTCCCGCAACGAGCGCAACCCTCGTTCTATGTTGCCAGCACGTGATGGTGGGGACTCATAGGAGA<br>CTGCCGGGGTCAACTCGGAGGAAGGTGGGGATGACGTCAAATCATCATCATGCCCCTTATGTCTAGGGCTGCA<br>AACATGCTACAATGCCGGTACAAAGGGCTGCGATACCGGAGGTGGAGCGAATCCAAAAAGCCGGTC<br>TCAGTTCGGATTGGGGTCTGCAACTCGACCCCCATGAAGTTGGAGTCGCTAGTAATCGCAGATCAGCAACG<br>CTGCGGTGAATACGTTCCCGGGCCTTGTACACACCGCCCGTCACGCCCATGAGAGTCGGTAACGCCCGAAG<br>CCGGTGGCCCAACCCTTGTGAGGGAGCCGTCGAAGGCGGATCGGCGATTGGGACGA |
| B/00176 | 2 | Micrococcus luteus | GATGAACGCTGGCGGCGTGCTTAACACATGCAAGTCGAACGATGAAGCCCAGCTTGCTGGGTGGATTAGT<br>GGCGAACGGGTGAGTAACACGTGAGTAACCTGCCCTTAACTCTGGGATAAGCCTGGGAAACTGGGTCTAA<br>TACCGGATAGGAGCGTCCACCGCATGGTGGGTGTTGGAAAGATTTATCCGGTTTGGATGGACTCGCGGCC<br>TATCAGCTTGTTGGTGGGGTAATGGCCTACCAAGGCGACGACGGGTAGCCGGCCTGAGAGGGTGACCGG<br>CCACACTGGGACTGAGACACGGCCCAGACTCCTACGGGAGGCAGCAGTGGGGAATATTGCACAATGGGC<br>GAAAGCCTGATGCAGCGACGCCGCGTGAGGGATGACGGCCTTCGGGTTGTAAACCTCTTTCAGTAGGGA<br>AGAAGCGAAAGTGACGGTACCTGCAGAAGAAGCACCGGCTAACTACGTGCCAGCAGCCGCGGTAATACG<br>TAGGGTGCGAGCGTTATCCGGAATTATTGGGCGTAAAGAGCTCGTAGGCGGTTTGTCGCGTCGTCTGTGA<br>AAGTCCGGGGCTTAACCCCGGGATCTGCGGTGGGTACGGGCAGACTAGAGTGCAGTAGGGGAGACTGGAA<br>TTCCTGGTGTAGCGGTGAAATGCGCAGATATCAGGAGGAACACCGATGGCGAAGGCAGGTCTCTGGGCT<br>GTAACTGACGCTGAGGAGCGAAAGCATGGGGAGCGAACAGGATTAGATACCCTGGTAGTCCATGCCGTA<br>AACGTTGGGCACTAGGTGTGGGGGACCATTCCACGGTTTCCGCGCCGCAGCTAACGCATTAAGTGCCCCGC<br>CTGGGGAGTACGGCCGCAAGGCTAAAACTCAAAGGAATTGACGGGGCCCGCACAAGCGGCGGAGCAT<br>GCGGATTAATTCGATGCAACGCGAAGAACCTTACCAAGGCTTGACATGTTCCCGATCGCCGTAGAGATAC<br>GGTTTCCCTTTGGGGCGGGTTCACAGGTGGTGCATGGTTGTCGTCAGCTCGTGTCGTGAGATGTTGGGT<br>TAAGTCCCGCAACGAGCGCAACCCTCGTTCCATGTTGCCAGCACGTAATGGTGGGGACTCATGGGAGACT |

TABLE 1-continued

SEQUENCE LISTING

Current application contains a Sequence Listing with 13 sequences and which are hereby incorporated by reference in its entirety. The 13 sequences are listed in Table 1. The full-length 16s nucleotide sequences of the purified bacterial strains of current invention are listed below and marked with a SEQ ID NO. Also the Deposit ID of each purified bacterial strain is noted in Table 1 with its corresponding 16S nucleotide sequence.

| Deposit ID | SEQ ID No | Organism (Genus species) | 16S nucleotide sequence (5'-3') |
|---|---|---|---|
| B/00214 | 3 | Kocuria rhizophila | GCCGGGGTCAACTCGGAGGAAGGTGAGGACGACGTCAAATCATCATGCCCCTTATGTCTTGGGCTTCACG<br>CATGCTACAATGCGACAATGGGTGCGATACTGTGAGGTGCAAGCCGTAATCCCAAAAGCCGTCTCA<br>GTTCCGATTGGGGTCTGCAACTCGACCCTGTGAAGTCGGAGTCGCTAGTAATCGCAGATCAGCAACGCTG<br>CGGTGAATACGTTCCCGGGCCTTGTACACACCGCCCGTCAAGTCACGAAAGTTGGTAACACCCGAAGCCG<br>GTGGCCTAACCCTTGTGGGGGAGCCGTCGAAGGTGGGGACCAGCCAGCGATTGGGACTA<br>GACGAACGCTGGCGGCGTGCTTAACACATGCAAGTCGAACGCTGAAGCTTGGTGCTTGCACTGGGTGA<br>TGAGTGGCGAACGGGTGAGTAATACGTGAGTAACCTGCCCTTGACTCTGGGATAAGCCTGGGAAACTGG<br>GTCTAATACTGGATACGACCATGTCACCGCATGGTGTGATGGTTTACTGGTTTTGGATGGC<br>TCACGGCCTATCAGCTTGTTGGTGGGGTAATGGCCTACCAGGCGACCGACGGGTAGCCGGCCTGAGAGG<br>GTGACCGGCCACACTGGGACTGAGACACGGCCCAGACTCCTACACGGGAGGCAGCAGTGGGGAATATTGCA<br>CAATGGGCGGAAGCCTGATGCAGCGACGCCGCGTGAGGGATGACGGCCTTCGGGTTGTAAACCTCTTTC<br>AGCACGGAAGAAGCGAAAGTGACGGTACGTGCAGAAGAAGCGCCGGCTAACTACGTGCCAGCAGCCG<br>GTAATACGTAGGGCGCAAGCGTTGTCCGGAATTATTGGGCGTAAAGAGCTCGTAGGCGGTTTGTCGCGTC<br>TGCTGTGAAAGCCCGGGGCTCAACCCCGGGTGTGCAGTGGGTACGGGCAGACTTGAGTGCAGTAGGGGA<br>GACTGGAATTCCTGGTGTAGCGGTGAAATGCGCAGATATCAGGAGGAACACCGATGGCGAAGGCAGGTC<br>TCTGGGCTGTTACTGACGCTGAGGAGCGAAAGCATGGGGAGCGAACAGGATTAGATACCCTGGTAGTCC<br>ATGCCGTAAACGTTGGGCACTAGGTGTGGGGGACAATTCCACGTTTTCCGCGCCGTAGCTAACGCATTAAG<br>TGCCCCGCCTGGGGAGTACGGCCGCAAGGCTAAAACTCAAAGGAATTGACGGGGGCCCGCACAAGCGG<br>CGGAGCATGCGGATTAATTCGATGCAACGCGAAGAACCTTACCAAGGCTTGACATACACCGGACACCGGCC<br>AGAGATGGTCTTTCCCCTTGTGGGCGGTGGTGTGTACAGGTGGTGCATGGTTGTCGTCAGCTCGTGTCGTGA<br>GATGTTGGGTTAAGTCCCGCAACGAGCGCAACCCTCGTTCTATGTTGCCAGCATGCCCTTCGGGGTGATGGG<br>ATAGGAGACTGCCGGGGTCAACTCGGAGGAAGGTGGGGATGACGTCAAATCATCATGCCCCTTATGTCTT<br>GGGCTTCACCGCATGCTACAAATGCCAGTACAATGGGTTGCGATACTGTGCGCCACCACGTGAGTCCTAGTAATCGCAGATC<br>GCTGTCTCAGTTCGATCGTCGTGGATAATCGCAGATCAAGTCACGAAAAGTTGGTAACA<br>AGCAACGCTGCGGTGAATACGTTCCCGGGCCTTGTACACACCGCCCGTCAAGTCACGAAAGTTGGTAACA<br>CCCGAAGCCGGTGGCCTAACCCTTGTGGGGGAGCCGTCGAAGGTGGCCGATTGGGACTA |
| B/00212 | 4 | Modestobacter marinus | TACCATGCAGTCGAGCGAGGCCATTCTTCGGGTGGTGCCTAGCGGCGAACGGTGAGTAACACGTG<br>GGCAACCTGCCCTCAGCTCTGGGATAACTCCAAGAAATTGTGCTAATACCGGATGTGACCGCTGACCGC<br>ATGGTCTGGTGGTGAAAGATTCATCGGCTGAGGATGGGCCCGCGGCCTATCAGCTTGTTGGTGGGGTA<br>ATGGCCCACCAAGGCGACGACGGGTAGCCGGCCTGAGAGGGTGACCGGCCACACTGGGACTGAGACAC<br>GGCCCAGACTCCTACGGGAGGCAGCAGTGGGGAATATTGCACAATGGGCGAAAGCCTGACGCAGCGAC<br>GCCGCGTGAGGGATGATGACCGCCTTCAGTAGGGACGAAGCGAAAGTGACGGTA<br>CCTACAGAAGAAGCACCCGGCTAACTACGTGCCAGCAGCCGCGGTAATACGTAGGGCGCAAGCGTTGTCC<br>GGAATTATTGGGCGTAAAGAGCTCGTAGGCGGTCTGTGTCAGGCTCAACCTGGGAACTGCTGAGTACTG<br>GGCCTGACGGCAGTCGATACGGAGGAACACCCGGTGGCCAAAACTAGAGTACTGCAGGGAGAACACACCGGTGGCGAAGGCGGTTCTCTGGACCCCCTGTGACGTACTACC<br>GAAAGCGTGGGAGCGAAACAGATTAGATACCCTGGTAGTCCACGCCGTAAACGTTGGGCGCTAGGTGT<br>GGGGGCCATTCCACGGCTCCGTGCCGCAGCTAACGCATTAAGCGCCCCGCCTGGGGAGTACGGCCGCA<br>AGGCTAAAACTCAAAGGAATTGACGGGGGCCCGCACAAGCGGCGGAGCATGTGGTTTAATTCGATGCAAC<br>GCGAAGAACCTTACCTAGGCTTGACATGCACATGAAATCTCGTAGAGATACGGAGATGTGGTTGGCCTGTG<br>CACAGGTGCTGCATGGCTGTCGTCAGCTCGTGTCGTGAGATGTTGGGTTAAGTCCCGCAACGAGCGCAAC<br>CCTCGTTCTTATGTTGCCAGCACGTCATGGTGGGGACTCATAGGAGACTGCCGGGGTCATCAACTCGGAGGAA |

TABLE 1-continued

SEQUENCE LISTING

Current application contains a Sequence Listing with 13 sequences and which are herebyincorporated by reference in its entirety. The 13 sequences are listed in Table 1. The full-length 16S nucleotide sequences of the purified bacterial strains of current invention are listed below and marked with a SEQ ID NO. Also the Deposit ID of each purified bacterial strain is noted in Table 1 with its corresponding 16S nucleotide sequence.

| Deposit ID | SEQ ID No | Organism (Genus species) | 16S nucleotide sequence (5'-3') |
|---|---|---|---|
| B/00210 | 5 | Kribbella qitaiheensis | GGTGGGGATGACGTCAAATCATCATGCCCCTTATGTCTAGGCTGCAAACATGCTACAATGGCCGGTACA<br>AAGGGCTGCCATACCGCGAGGTGGAGCGAATCCAAAAGCCGGTCTCAGTTCGATTCGGGTCTGCAA<br>CTCGACCCCATGAAGTTGGAGTCGCTAGTAATCGCAGATCAGCAACGCTGCGTGAATACGTTCCCGGGC<br>CTTGTACACACCGCCCGTCACGTCACGAAAGTCGGTAACGCCCGAAGCCGGTGGCCCACCCTTGTGAG<br>GGAGCCGTCGAAGCG<br>GACGAACGCTGGCGGCGTGCTTAACACATGCAAGTCGAGCGGTAAGGCTCCTTCGGGAGGTACACGAGCG<br>GCGAACGGGTGAGTAACACGTGAGCAACCTACCCTCAACTTCGGGATAAGCCTCGGAAACGGGGTCTAAT<br>ACCGGATATCACTCTTGGTTCATGACCGGGGTTGAAAGTTCGGCGGTTGGGGATGGGCTCGCGGCCT<br>ATCAGCTTGTTGGTGGGGTAATGGCCTACCAAGGCGACGACGGGTAGCCGGCCTGAGAGGGCGACCGGC<br>CACACTGGGACTGAGACACGGCCCAGACTCCTACGGGAGGCAGCAGTGGGGAATATTGCCAATGGGCG<br>AAAGCCTGACGCAGCAACGCCGCGTGAGGGATGACGGCCTTCGGGTTGTAAACCTCTTTCAGCAGGAC<br>AGGGTCCGAGCGTTGTCCGGAATTATTGGGCGTAAAGGCTCGTAGGCGGTTGTCACGTCGGGAGTGA<br>AAACTCGGAGCTTAACTCCGAGATATTCGGAATGCTGCAGATCGGTAAACTAGAGTTCGGTAGGGGA<br>CTCCTGGTGTAGCGGTGAAATGCGCAGATATCAGGAGGAACAGGCCGTGGCCGAAGGCGCTCTGGGCC<br>TACCTGACGCTGAGGAGCGAAAGCGTGGGGAGCGCAACAGGATTAGATACCCTGGTAGTCCACGCCGTAA<br>ACGTTGGGCTCTAGGTGTGGGGAACATTCCACGTCCTGCCGTGCCGTAAGGCTAAACGCATTAAGCCCCGC<br>CTGGGGAGTACGGCCGCAAGGCTAAAACTCAAAGGAATTGACGGGGGCCCGCACAAGCGGCGGAGCAT<br>GCGGATTAATTCGATGCAACGCGAAGAACCTTACCTGGGTTTGACATATAGAGGAAATCCTCCAGAGATGG<br>GGGTCCCTTCGGGGCCTCTATACAGGTGGTGCATGGCTGTCGTCAGCTCGTGTCGTGAGATGTTGGGTTAA<br>GTCCCGCAACGAGCGCAACCCTCGTCCTATGTTGCCAGCACGTTATGGTGGGGACTCATAGGAGACTGCC<br>GGGGTCAACTCGAGGAAGGTGGGGATGACGTCAAGTCATCATCATGCCCCTTATGTCCAGGGCTTCACGCAT<br>GCTACAATGGCCGGTACAAAGGGCTGCGATAGTGCGACCCGAAGCCGAATCCCAAAAAGCCGGTCTCAGT<br>TCGGATTGGGGTCTGCAACTCGACCCCATGAAGTCGGAGTCGCTAGTAATCGCAGATCAGCAACGCTGCG<br>GTGAATACGTTCCCGGGCCTTGTACACACCGCCCGTCAAGTCACGAAAGTCGGCAACACCCGAAGCCGGT<br>GGCCTAACCCTTGTGAGGGAGCCGTCGAAGGTGGGCGTTGGCGATTAGGACGA |
| B/00211 | 6 | Nocardiopsis dassonvillei | TTACCATGCAGTCGAGCGGTAAGGCCCTTCGGGGTAAGGCTACACGAGCGCGGACGGGTGAGTAACACGTGAGC<br>AACCTGCCCCTGACTCTGGGATAAGCGCTGGAAACGCGTCTAATACCGGATACGACCCCTACCTCATG<br>GTGAGGGTGGAAAGTTTTTCGGTCAGGGATGGCTCGCGGCCTATCAGCTTGTTGGTGGGGTAACGGC<br>CTACCAAGGCGATTACGGTAGCCGGCCTGAGAGGGCGACCGGCCACACTGGGACTGAGACACGGCCCA<br>GACTCCTGCGGAGGCAGCAGTGGGGAATATTGCGCAATGGGCGAAAGCCTGACGCAGCGACGCCGCG<br>TGGGGGATGACGGCCTTCGGGTTGTAAACCTCTTTCACCACCAACGGCAAGCCTTCCAGTTCTCTGGAGGTT<br>GACGCTAGGTGGAGAATAAGGACCGGCTAACTACGTGCCAGCAGCCGCGGTAATACGTAGGGTCCGAGC<br>GTTGTCCGGAATTATTGGGCGTAAAGAGCTCGTAGGCGGCGTGTCGCCTGTCGTGTAAAGACCGGGGC<br>TTAACTCCGGTTCTGCAGTGATACGGGCATGCTAGAGTTAGGGAGGGAATTGGAATTCCTGGTGTAG<br>CGGTGAAATGCGCAGATATCAGGAGGAACACCGGTGGCGAAGGCGGGTTCTCTGGGCCTTACCTGACGCT<br>GAGGAGCGAAAGCATGGGTAGCGAACAGGATTAGATACCCTGGTAGTCCATGCCGTAAACGTTGGGCG<br>CTAGGTGTGGGACTTTCCACGGTTTCCGCGCCGTAGCTAACGCATTAAGCGCCCCGCCTGGGGAGTAC<br>GGCCGCAAGGCTAAAACTCAAAGGAATTGACGGGGGCCCGCACAAGCGGCGGAGCATGTGGATTAATTC<br>GATGCAACGCGAAGAACCTTACCAAGGCTTGACATCACCCGTGACTCGCAGAGATGTGAGGTCATTTAG<br>TTGGCGGTGAAGACCGTGTCAGCGCGGTGTCGTCAGCTCGTGTCGTGAGATGTTGGGTTAAGTCCCGCAA<br>GACGCAACCCTTGTTCTATGTTGCCAGCACGTAATGGTGGGGACTCATGGGAGACTGCCGGGGTCAA<br>CGAGCGCAACCCCTTGTCTATGTTGCCAGCACGTAATGGTGGGGACTCATGGGAGACTGCCGGGGTCAA |

TABLE 1-continued

SEQUENCE LISTING

Current application contains a Sequence Listing with 13 sequences and which are hereby incorporated by reference in its entirety. The 13 sequences are listed in Table 1. The full-length 16S nucleotide sequences of the purified bacterial strains of current invention are listed below and marked with a SEQ ID NO. Also the Deposit ID of each purified bacterial strain is noted in Table 1 with its corresponding 16S nucleotide sequence.

| Deposit ID | SEQ ID No | Organism (Genus species) | 16S nucleotide sequence (5'-3') |
|---|---|---|---|
| B/00216 | 7 | Streptomyces graminofaciens | CTCGGAGGAAGGTGGGGATGGATGCTCAAGTCATGCCCCTTATGTCTTGGGCTGCAAACATGCTACAAT<br>GGCCGGTACAATGGGCGGTGCGATACCGTAAGGTGCGAGCGAATCCTAAAAGCCGGTCTCAGTTCGGAT<br>GGGGTCTGCAACTCGACCCCATGAAGTCGAGTCCTAGTAATCGCAGATCAGCAACGCCGGGTG<br>CACATGCAAGTCGAACGATGAAGCCCTTCGGGGTGATTAGTGGCGAACGGGTGAGTAACACGTGGGCA<br>ATCTGCCCTTCACTCTGGGACAAGCCCTGGAAACGGGGTCTAATACCGGATATAACACTCGGATCGCATGG<br>TCTCGCGGTTGAAAGCTCCGGCGGTTGAAGGATGAGCCCGCGGCCTATCAGCTTGTTGGTGGGGTGATGGC<br>CTACCAAGGCGACGACGGGTAGCCGGCCTGAGAGGGTGACCGGCCACACTGGGACTGAGACACGGCCC<br>AGACTCCTACGGGAGGCAGCAGTGGGGAATATTGCACAATGGGCGAAAGCCTGATGCAGCGACGCCG<br>TGAGGGATGACGGCCTTCGGGTTGTAAACCTCTTTCAGCAGGGAAGAAGCGAAAGTGACGGTACCTGCA<br>GAAGAAGCGCCGGCTAACTACGTGCCAGCAGCCGCGGTAATACGTAGGGCGCAAGCGTTGTCCGGAATT<br>ATTGGGCGTAAAGAGCTCGTAGGCGGCTTGTCACGTCGGATGTGTAGGGCGCTTAACCCCGGGTC<br>TGCATTCGATACGGGCAGGCTAGAGTGTGGTAGGGGAGATCGGAATTCCTGGTGTAGCGGTGAAATGCG<br>CAGATATCAGGAGGAACACCGGTGGCGAAGGCGGATCTCTGGGCCATTACTGACGCTGAGGAGCGAAAG<br>CGTGGGGAGCGAACAGGATTAGATACCCTGGTAGTCCACGCCGTAAACGTTGGGAACTAGGTGTTGGCG<br>ACATTCCACGTCGTCGTGCCGCAGCTAACGCATTAAGTTCCCCGCCTGGGGAGTACGGCCGCAAGGCTA<br>AGAACTCAAAGGAATTGACGGGGGCCCGCACAAGCAGCGGAGCATGTGGCTTAATTCGACGCAACGCGAA<br>GAACCTTACCAAGGCTTGACATATACCGGAAAGCATCAGAGATGGTGCCCCCTTGTGGTCGGTATACAG<br>GTGGTGCATGGCTGTCGTCAGCTCGTGTCGTGAGATGTTGGGTTAAGTCCCGCAACGAGCGCAACCCTTG<br>TTCTGTTGCCAGCATGCCCTTCGGGGTGATGGGGACTCACAGGAGACTGCCGGGGTCAACTCGGAGG<br>AAGGTGGGGACGACGTCAAGTCATCATGCCCCTTATGTCTTGGGCTGCACACGTGCTACAATGGCCGGTA<br>CAAAGAGCTGCGAGCGGGTGACGGATCATCTCAAAAAGCCGGTCTCAGTTCGGATTGGGGTCTGC<br>AACTCGACCCCATGAAGTCGGAGTTGCTAGTAATCGCAGATCAGCATTGCTGCGGTGAATACGTTCCCG<br>GGCCTTGTACACACCGCCCGTCACGTCACGAAAGTCGGTAACACCCGAAGCCGGTGGCCCAACCCCTTGTG<br>GGAGGGAGCTGTCGAAGTGACCT |
| B/00209 | 8 | Streptomyces ramulosus | ATTCGACGATTCCCCCACAAGGGGTTGGGCCACCGGCTTCGGGTGTTACGACTTTCGTGACGTGACG<br>GGCGGTGTGTACAAGGCCCGGGAACGTATTCACCGCAGCATGCTGATCTGCGATTACGAACTCCAA<br>CTTCATGGGGTCGAGTTGCAGACCCCAATCGAACTGAGACCGGCTTTTGAGATTCGCTCCACCTCACG<br>GCTTCGCAGCTCCATTGTACCGGCCATTGTACCACGTGTCAGCCCAAGACATAAGGGGCATGATGACTTG<br>AGTGCCTCCCCATTCTCCCAGTTGACCCGGACTCCGTGAGTCCCATCACCCCGAAAGGCAT<br>GCTGGCAACACAGAACACCTGTACACCGACCACAAGGGGGCGCCCTGTCTCCAGACGTTTCCGGTGTATGTCAA<br>ACAGCCATGCACCATGTCTTCGCTGCCGTGCCACCGGCGAATTAAGCCACATGCTCCGGTCCTTGCGGCCCCGTCA<br>ATTCCTTTGAGTTTTAGCCTTGCGGCCGTATCTCCCAGGCGGGAACTTAATGCGTTAGCTGCGGCACGG<br>ACAACGTGGAATGTCGCCCACAGCTTTCGCTTCGCTCCAGCGTCAGTATCGGCCAGAGATCCCCAGAACTCGCTCCACCGGTGTTCCTC<br>TCGATATCTGCGCATTTCACCGCTACCAGGAATTCCAAGACCCTCGTACCGAACTCTAGCCTGCCCGTAT<br>CGAATGCAGACCCGGTTAAGCCCCGGCTTTCACATCCGACCAAGCCGCCTACGAGCTCTTTAC<br>GCCCAATAATTCCGGACAACGCTTGCGCCTACGCTTCCCTGCGAAAGAGTTTACAACCCGAAGGCCGTCATCC<br>TTCTTCTGCAGGTACCGTCGCTGCTACTCTGCCTCATCAGGCTTTGCCCCATTGTGCAATATTCCCCACTGCTGCCCTCCCGTAGGAG<br>TCTGGGCCGTCGTCCAGTCGCATCAGGTTTGCGGCATAGCCCCAGTTAGCACGTAGTTAGCCGGCGC<br>GGCCATCACCCCACCAACAAGCTGATAGGCCCGGCTCATCCTGCACCGCCGAGCTTTCCACCACCAG |

TABLE 1-continued

SEQUENCE LISTING

Current application contains a Sequence Listing with 13 sequences and which are hereby incorporated by reference in its entirety. The 13 sequences are listed in Table 1. The full-length 16S nucleotide sequences of the purified bacterial strains of current invention are listed below and marked with a SEQ ID NO. Also the Deposit ID of each purified bacterial strain is noted in Table 1 with its corresponding 16S nucleotide sequence.

| Deposit ID | SEQ ID No | Organism (Genus species) | 16S nucleotide sequence (5'-3') |
|---|---|---|---|
| B/00208 | 9 | Crossiella cryophila | ACCATGCGCCGGTAGTCATATCCGGTATTAGACCCCGTTTCCAGGGCTTGTCCAGAGTGCAGGGCAGATTGCCCACGTGTTACTCACCCGTTGCCACTAATCCCCACCGAAGTCGGGTTCATCGTTCGACTTGCATGGT<br>GCTTGGTGCTGGTGGAAAGTTCCGGCCGCGTGCAGGATGGCCCGCGGCCTATCCAGCTTGTTGTGGGTAATG<br>GCCTACCAAGGCGACGACGGGTAGCCGCCGCCAAGGGGCAGCCGGCCACCACTGGACCTGAGACACGCGC<br>CCAGACTCCTACGGGAGGCAGCAGTGGGGAATATTGCGCAATGGGCGAAAGCCTGACGCAGCGACGCCG<br>CGTGAGGGATGACGGCCTTCGGGTTGTAAACCTCTTTCAGTGCCGACGAAGCGAAAGTGACGGTAGGTA<br>CAGAAGAAGCACCGGCCAACTACGTGCCAGCAGCCGCGGTAATACGTAGGGTGCGAGCGTTGTCCGGAA<br>TTATTGGGCGTAAAGAGCTCGTAGGCGGCTTGTTGCGTCGGGTGTGAAAACTCGGGGCTCAACTCTGAGC<br>TTGCAGTCGATACGGCCAGACATCCGAGTTCGGCGAAGGGAGACTGGAATTCCTGGTGTAGCGGTGAAATGC<br>GCAGATATCAGGAGGAACAGACCGATTAGATACCGGTAGTCCACGCCGTAAACGTTGGGCGTAGGTGTGGG<br>AGCGTGGGAGCGGAACAGGATTAGATACCCTGGTAGTCCACGCCGTAAACGTTGGGCGTAGGTGTGGG<br>GGTCATTCCACGGCCTCCGTGCCGCAGCTAACGCATTAAGCGCCCCGCCTGGGAGTACGGCCGCAAGG<br>CTAAAACTCAAAGGAATTGACGGGGGCCCGCACAAGCGGCGGAGCATGTGGATTAATTCGATGCAACGC<br>GAAGAACCTTACCTGGCTTGACATACACCGGAAACCTGCAGAGATGTTGGGTTAAGTCCCGCAACGGCAACC<br>CAGGTGGTGCATGGCTGTCGTCAGCTCGTGTCGTGAGATGTTGGGTTAAGTCCCGCAACGAGCGCAACC<br>CTCGTTCCATGTTGCCAGCCGCGTAATGGCGGGACTCATGGGAGACTGCCGGGGTCAACTCGGAGGAAG<br>GTGGGGATGACGTCAAGTCATCATCATGCCCCTTATGTCCAGGGCTTCACAGGCTACAACGTGCTACAA<br>TGGGCTGCTAAGCCGTGAGGTGGAGTCGCTAGTAATCGCAGATCAGCAACGCTGCGGTGAATACGTTCCCGGGCC<br>TCGACCCCGTGAAGTTGGAGTTGCCTAGTAATCGCAGATCAGCAACGCTGCGGTGAATACGTTCCCGGGCC<br>TTGTACACACCGCCCGTCACGTCACGAAAGTCGTAACAAGGTAGCCGTAACCCGGAAGGG<br>GGGAGTGTGA |
| B/00188 | 10 | Micromonospora carbonacea | ATTCGACGGCTCCCTCCTCCACAAGGGTTGGGCCACCGGCTTCGGGTGTTGCCGACTTTCGTGACGTGACGG<br>GCGCAGTTCGTGTACAAGGCCCGGAACGGTATTCACCGCAGCGTTGCTGATCTGCAGTTACTAGCGACTCCGAC<br>TTCACGGGTTCAGACCGAACCCATGAGACCCGAACTGAGACAACGGCCTTTTGGGATTCGCTCACCTCACGG<br>TATCCAGCCCATTGTACCCGGCAGCTCCCCTCCCGAGTTAGCATGCGTGAAGCCCTGGACATAAGGGGCATGATGACTTGA<br>CGTCATCCCACCACCTTCCTCCGAGTTGACCCCGGCAGCTTCACCACATCTTCCAACACATCTCACGACAGAGCGCTGGACATAACGGCTGGCAA<br>CATCGAACGAGGGTTGCGCTCGTTGCGGGACTTAACCCAACATCTCACAGGCTTTGCGCGACCATGTCAAACCAGGGCCAT<br>GCACCACCTGACGCCCCGAAGGACCCCCCATCTCTGAGGGTTTGCGCGACCATGTCAAACCAGGTA<br>AGGTTCTTCGCGTTGCGGCTCGGCGTACTCCCAGGCGGGCCCTAATGCGTTAGCGTCGGCACAGAGGAACCGGA<br>GTTTAGCCGTTCGCGGCTACTCCCAGGCGGGGCCCTAATGCGTTAGCGTCGGCACAGAGAACCGGA<br>GAGGCCCCCACACCTGCCCCAACGTTTACAGCGGGACTACCAGGGTATCTAATCCTGTTCGCTCCC<br>CACGCTTTCGCTCCTCAGCGTCAGTATCGGCCAGAGACCCGCCTTCGCCACCGGTGTTCCTCCTGATATC<br>TGCGCATTTCACCGCTACACCAGGAATTCCACCGTGACGCGACAAGCCGCCACCTCAGCCTCTTTACGCCCAATA<br>GGCTTGGGTTGAGCCCAAGTTTTCACCGTGACGCGACAAGCCGCCATAGTTGGCCGGGCGCTTCTTCTG<br>AATCCGGACAACCGCTTCGCCGTCTGCCCCTGCGAAAGAGGTTTACAACCCGAGCCGCTCATCCTCACGC<br>CAGGTACCGTCATCAGGCTTCCGCCCATTGTCAATATTGCCCCTCAGGCCGCTACCCTGTCCTCCCTAGGAGTCGGGC<br>CGTGTCGCTCAGTGGCCGGCGTGTGCCCGGTGCGCCCTTCACCCGCTACCCGTGCTCCCCGTCGCCGTTGGTAGGCATC<br>ACCCCACCAACAAGCTGATTAGGCCCGCGACCCATCCAGGCCAGCGGAAAAACTTTCCACCCCAGTCATGCGA<br>CCAAAGGTTTATCCGGTATTAGCCCCCCGTTTCCGAGGGTTATCCCAAAGCCCTAGGCAGGTTGCTCACG<br>TGTTACTCACCCGTTCGCCGTTGAGTACCCCGAAGGGCCTTCCGCTCGACTTGCATGG |

TABLE 1-continued

SEQUENCE LISTING

Current application contains a Sequence Listing with 13 sequences and which are hereby incorporated by reference in its entirety. The 13 sequences are listed in Table 1. The full-length 16S nucleotide sequences of the purified bacterial strains of current invention are listed below and marked with a SEQ ID NO. Also the Deposit ID of each purified bacterial strain is noted in Table 1 with its corresponding 16S nucleotide sequence.

| Deposit ID | SEQ ID No | Organism (Genus species) | 16S nucleotide sequence (5'-3') |
|---|---|---|---|
| B/00181 | 11 | Streptomyces camponoticapitis | TTCGACGCTCCTCCCACAAGGGGTTGGGCACCGGCTTCGGGTGTTACCGACTTTCGTGACGTGACGGG<br>CGGTGTGTACAAGGCCCGGGAACGTATTCACCGCAGCAATGCTGATCTGCGATTACTAGCAACTCCGACT<br>TCATGGGGTCGAGTTGCAGACCCCAATCGAACTGAGACCGGCTTTTTGAGATTCGCTCCACCTTGCGGT<br>ATCGCAGCTCATTGTACCGGCCATTGTAGCACGTGTGCAGCCCAAGACATAAGGGGCATGATGACTTGAC<br>GTCGTCCCACCTTCCTCCGAGTTGACCCCGGCAGTCTCCTGTGAGTCCCCATCACCCCGAAGGGCATGC<br>TGGCAACACAGAACAAGGGTTGCGCTCGTTGCGGGACTTAACCCAACATCTCACACGAGCTGACGAC<br>AGCCATGCACCACTGTACACCGACCACAAGGGGGCACCATCTCTGATGCTTTCCGGTGTATGTCAAGC<br>CTTGGTAAGGTTCTTCGCGTTGCGTCGAATTAAGCACCACATGCTCCGCTGCCTTGTGCGGGCCCCGTCAATT<br>CCTTTGAGTTTTAGCCTTGCGCCGTATCCCCAGGCGGGGAACTTAATGCGTTAGCTGCGGCACCGACG<br>ACGTGGAATGTCGCCAACACCTAGTTCCCAACGTTTCCCAACGTGACTACCAGGGTATCTAATCCTGTTCG<br>CTCCCACGCTTTCGCTCCTCAGCGTCAGTAATGCCCAGAGATCCGCCTTCGCCACCGGTGTTCCTCCTG<br>ATATCTGCGCATTTCACCGCTACACCAGGAATTCCGATCTCCCCTACCACACTCTAGTCTGCCCGTATCGA<br>ATGCAGACCCGGGGTTAAGCCCGGGCTTTCACACCGACGTGACAAACCGCTACGAGCTCTTTACGCC<br>CAATAATTCCGGACAACGCTTGCGCCCTACGTATTACCGCGGCTGCTGGCACGTAGTTAGCCGGCTTC<br>TTCTGCAGTACCGTCACTTTCGCTTCTTCCCTGCTGAAAGAGGTTTACAACCCGAAGGCCGTCATCCCTC<br>ACGCGCGTCGCTGCTGCATCAGGCTTTCGCCATTGTGCAATATTCCCCACTGCTGCCTCCCGTAGGAGTCT<br>GGGCCGTGTCTCAGTCCCAGTGTGGCCGGTCACCCTCTCAGGCCGGCTACCCGTCGTCGCCCTTGGTAGG<br>CCATTACCCCACCAACAGTATTATCCGGTATTAGACCCGGCTTTCCCCACTAATCCACCCGAAGGCTTTTAACCATCCCC<br>ATGAGGGGCACAGTATTATCCGGTATTAGACCCGCTATTAGACCGCTGTGCCCAGAGTGCAGGGCAGATTG<br>CCCACGTGTTACTCACCCGTTCGCCACTAATCCACCCGAAGGCTTCATCGTTGACTTGCATG |
| B/00186 | 12 | Streptomyces caeruleus | AAGCTCCCTCCCACAAGGGGTTGGACCACCGGCTTCGGGTGTTACCGACTTTCGTGACGTGACGGCGG<br>TGTGTACAAGGCCCGGGAACGTATTCACCGCAGCAATGCTGATCTGCGATTACTAGCAACTCCGACTTCAT<br>GGGGTCGAGTTGCAGACCCCAATCGAACTGAGACCGGCTTTTTGAGATTCGCTCCACCTTGCGGTATCG<br>CAGCTCATTGTACCGGCCATTGTAGCACGTGTGCAGCCCAAGACATAAGGGGCATGATGACTTGACGTCG<br>TCCCCACCTTCCTCCGAGTTGACCCCGGCAGTCTCCTGTGAGTCCCCATCACCCCGAAGGGCATGCTGGC<br>AACACAGAACAAGGGTTGCCGCTCGTTGCGGGACTTAACCCAACATCTCACGACACGAGCTGACGACACC<br>ATGCACCACCTGTACACCGACCACAAGGGGGCACCATCTCTGATGCTTTCCGGTGTATGTCAAGCCTTG<br>GTAAGGTTCTTCGCGTTGCGTCGAATTAAGCCACATGCTCCGCTGTTGTGCGGGCCCCGTCAATTCCTT<br>TGAGTTTTAGCCTTGCGGCCGTACTCCCCAGGCGGGAACTTAATGCGTTAGCTGCGGCACCGACGACGT<br>GGAATGTCGCCAACACCTAGTTCCCAACGTTTACGGCGTGGACTACCAGGGTATCTAATCCTGTTCGCTCC<br>CCACGCTTTCGCTCCTCAGCGTCAGTAATGGCCAGAGATCCGCCTTCGCCACCGGTGTTCCTCCTGATAT<br>CTGCGCATTTCACCGCTACACCAGGAATTCCGATCTCCCCTACCACACTCTAGTCTGCCCGTATCGAATGC |

TABLE 1-continued

SEQUENCE LISTING

Current application contains a Sequence Listing with 13 sequences and which are herebyincorporated by reference in its entirety. The 13 sequences are listed in Table 1. The full-length 16S nucleotide sequences of the purified bacterial strains of current invention are listed below and marked with a SEQ ID NO. Also the Deposit ID of each purified bacterial strain is noted in Table 1 with its corresponding 16S nucleotide sequence.

| Deposit ID | SEQ ID No | Organism (Genus species) | 16S nucleotide sequence (5'-3') |
|---|---|---|---|
| | | | AGACCCGGGTTAAGCCCTTCACCCCAGACGTGACAAACCGCTTCACGAGCTCTTTACGCCCAAT<br>AATTCCGGACAACGCTTGCGCCTTACGTATTACCGGGCTGTGCACGTAGTTAGCCGGCGCTTCTTCT<br>GCAGGTACCGTCACTTTCGCTTCTTCCCTGCTGAAAGAGGTTTACAACCCGAAGGCCGTCATCCCTCACGC<br>GGCGTCGCTGCATCAGGCTTTCGCCCATTGTGCAATATTCCCACTGCTGCCTCCCGTAGGAGTCTGGGC<br>CGTGTCTCAGTCCAGTGTGGCCGGTCGCCTTCAGGCCGCTACCCGTCGTCGCTTGGTAGGCCATT<br>ACCCCACCAACAAGCTGATAGGCCGGGCTCATCCTGCACCGCCGGAGCTTTCAACCGTCCCCATGAG<br>GGGCACAGTATTATCCGGTATTAGACCACCCCGTTTCCAGGGCTTGTCCCAGAGTGCAGGGCAGATTGCCCAC<br>GTGTTACTCACCCGTTCGCCACTAATCACCCGAAGGCTCATCGTTCGACTCGAGGTAAG |
| B/00187 | 13 | Micromonospora eburnea | CTATTCGACGGCTCCCTCCACAAGGGTTGGGCCACCGGCTTCGGGTGTTGCCGACTTTCGTGACGTGACG<br>GGCGGTGTGTACAAGGCCCCGGAACGTATTCACCCGAGCGTTGCTGATCGCTGGATTAGCGACTCCGA<br>CTTCACGGGGTCGAGTTGCAGACCCCGATCGAACTGAGACCGGCTTTTTGGGATTCGCTCCACCTCACG<br>GTATCGCAGCCCATTGTACCGGCCATTGTAGCATGCGTGAAGCCTGGACATAAGGGCATGATGACTTG<br>ACGTCATCCCCACCTTCTCCGAGTTGACGTCGGCCAGTCTTCGATGAGTCCCCCATAACGCGCTGGCA<br>ACATCGAACGAGGGTTGCGCTCGTTGCGGGACTTAACCCAACATCTCACGACACGACAGCCA<br>TGCACCACCTGTGACCGCCCCCGAAGGACCCCATCTCTGCAGGTTTGCGCGCCATGTCAAACCCAGT<br>AAGGTTCTTCGCGTTGCATCGAATTAATCCGCATGCTCCCGCGTTGTGCGGGCCCCGTCAATTCCTTTG<br>AGTTTAGCCTTGCGGCCGTACTCCCAGGCGGGGCGCTTAATGCGTTAGCTGCGGCACAGGAACCGG<br>AGAGCCCCCACACCTAGCGCCCAACGTTACAGCGTGACTACGGCTGGTACACCAGGGTATCTAATCCTGTTCGCTCC<br>CCAGCCTTTCGCTCCTCAGCGTCAGTATGCCCAGAGACCCGCCTTCGCCACCGGTGTTCCTCCTGATAT<br>CTGCGCATTTCACCGCTACACCAGGAATTCCAGTCTCCCTACAGCGACAAGCCGCTACGAGCTCTTTACGCCCAAT<br>AGGCCCGCGGTTGAGCCCGGGGTTTTCACAGTCGACGCGACAAGCCGCTACGAGTCCTTTACGCCCAAT<br>AAATCGGACAACGCTCGCGCCCTACGTCTTACCGGCGCTGCTGCACGTAGTTGGCCGGCGCTTCTTCT<br>GCAGGTACCGTCACTTACGCTTCGTCCCTCTGAAAGA |

The invention claimed is:

1. A synthetic composition comprising a plant element and a heterologous disposed bacterial strain, wherein said bacterial strain comprises at least one 16S nucleotide sequence that is at least 99% identical to SEQ ID NO: 7 and wherein the synthetic composition is capable of improving plant growth and/or yield as compared to a reference plant element not further comprising the bacterial strain.

2. A method of improving plant growth and/or yield, comprising the step of treating a plant element with a purified bacterial strain in an amount effective to increase the growth and/or yield in the plant derived from the treated plant element relative to a plant derived from a reference plant element, wherein said bacterial strain comprises at least one 16S nucleotide sequence that is at least 99% identical to SEQ ID NO: 7.

3. The synthetic composition according to claim 1, wherein the plant element is a plant seed.

4. The synthetic composition according to claim 1, wherein the bacterial strain comprises at least one 16S nucleotide sequence that is identical to SEQ ID NO: 7.

5. The synthetic composition according to claim 1, wherein the bacterial strain is deposited with the Polish Collection of Microorganisms, under the terms of the Budapest Treaty, as Deposit ID: B/00216.

6. The synthetic composition according to claim 1, wherein the bacterial strain is disposed on the plant element in an amount of at least 100 CFU.

7. A method of preparing the synthetic composition according to claim 3, the method comprising the step of mechanically or manually inoculating a plurality of plant seeds with a purified bacterial strain, wherein said bacterial strain comprises at least one 16S nucleotide sequence that is at least 99% identical to SEQ ID NO: 7.

8. The method according to claim 7, wherein the bacterial strain comprises at least one 16S nucleotide sequence that is identical to SEQ ID NO: 7.

9. The method according to claim 7, wherein the bacterial strain is deposited with the Polish Collection of Microorganisms, under the terms of the Budapest Treaty, as Deposit ID: B/00216.

10. The method according to claim 2, wherein the plant element is a plant seed.

* * * * *